US006274726B1

(12) United States Patent
Laugharn, Jr. et al.

(10) Patent No.: US 6,274,726 B1
(45) Date of Patent: Aug. 14, 2001

(54) PRESSURE-ENHANCED EXTRACTION AND PURIFICATION

(75) Inventors: James A. Laugharn, Jr., Winchester; Robert A. Hess, Cambridge; Feng Tao, Boston, all of MA (US)

(73) Assignee: BBI Bioseq, Inc., West Bridgewater, MA (US)

( * ) Notice: Subject to any disclaimer, the term of this patent is extended or adjusted under 35 U.S.C. 154(b) by 0 days.

(21) Appl. No.: 09/016,062

(22) Filed: Jan. 30, 1998

Related U.S. Application Data

(63) Continuation-in-part of application No. 08/962,280, filed on Oct. 31, 1997, now Pat. No. 6,111,096.

(51) Int. Cl.[7] .................................................. C07H 21/00
(52) U.S. Cl. ..................... 536/25.4; 536/25.41; 422/99; 203/1; 203/2; 203/34; 203/35; 203/193; 203/194; 203/298.25; 203/400; 203/403
(58) Field of Search .......................... 536/25.4, 25.41; 422/99; 203/1, 2, 34, 35, 193, 194, 298.25, 400, 403

(56) References Cited

U.S. PATENT DOCUMENTS

| | | | |
|---|---|---|---|
| 3,609,252 | * | 9/1971 | Broce et al. ............... 179/100.41 T |
| 4,323,439 | | 4/1982 | O'Farrell ............................. 204/180 |
| 5,003,047 | * | 3/1991 | Yarmush et al. . |
| 5,346,999 | | 9/1994 | Cathcart et al. ................... 536/25.41 |
| 5,596,092 | | 1/1997 | Schneider ............................. 536/25.4 |
| 5,605,839 | | 2/1997 | Simpson et al. ......................... 436/89 |
| 5,606,046 | | 2/1997 | Woodard et al. .................... 536/25.4 |
| 5,610,290 | | 3/1997 | Woodard et al. .................... 536/25.4 |
| 5,610,291 | | 3/1997 | Woodard et al. .................... 536/25.4 |
| 5,616,701 | | 4/1997 | Woodard et al. .................... 536/25.4 |
| 5,637,687 | | 6/1997 | Wiggins ............................... 536/25.4 |
| 5,650,506 | | 7/1997 | Woodard et al. .................... 536/25.4 |
| 5,700,639 | | 12/1997 | Trauth et al. ............................. 435/6 |
| 5,707,812 | | 1/1998 | Horn et al. ................................ 435/6 |
| 5,934,766 | * | 8/1999 | Feigel et al. ....................... 303/119.2 |
| 6,036,923 | * | 3/2000 | Laugharn et al. . |

FOREIGN PATENT DOCUMENTS

| | | |
|---|---|---|
| 0 127 327 | 12/1984 | (EP) . |
| WO97/31105 | 8/1997 | (WO) . |

OTHER PUBLICATIONS

Mozhaev et al., "Exploiting the effects of high hydrostatic pressure in biotechnological applications", *TIBTECH*, vol. 12, pp. 493–501, (1994).
Bollag, Daniel M., "Protein Extraction and Solubilization", *Protein Methods*, 2nd ed., pp. 27–49, 1996.
Madou, Marc I., "Fluid Propulsion Mechanisms" and "Thermal Actuators", *Fundamentals of Microfabrication*, pp. 431–434, 439–441, 446–447, 1997.
"Mini–Bomb Cell Distrupion Chamber" "Ultrasonicators", *Kontes*, Catalog, pp. 46, 356, 1992.
Carter, M.J. et al., "An Inexpensive and Simple Method for DNA Purifications on Silica Particles", *Nucleic Acids Research*, vol. 21, No. 4, p. 1044, 1993.
"Isolation of RNA from Plant Cell Suspension Cultures and Calli by Sonication", *BioTechniques*, vol. 23, No. 6, pp. 996–1000, 1997.
Wages, Jr., J.M. et al., "Affinity Purification of RNA: Sequence–Specific Capture by Nonionic Morpholino Probes", *BioTechniques*, vol. 23, No. 6, pp. 1116–1121, 1997.
Boyle, J.S., et al., "An Inexpensive Alternative to Glassmilk for DNA Purification", *Trans. Genet.*, 11(1):8, 1995.
Burke et al., "Microfabrication Technologies for Integrated Nucleic Acid Analysis," *Genome Research*, 7:189–197, 1977.

* cited by examiner

*Primary Examiner*—James O. Wilson
(74) *Attorney, Agent, or Firm*—Fish & Richardson P.C.

(57) ABSTRACT

The invention is based on the discovery that hyperbaric, hydrostatic pressure reversibly alters the partitioning of biomolecules between certain adsorbed and solvated phases relative to partitioning at ambient pressure. The new methods and devices disclosed herein make use of this discovery for highly selective and efficient, low salt isolation and purification of nucleic acids from a broad range of sample types, including forensic samples, blood and other body fluids, and cultured cells.

In one embodiment, the invention features a pressure-modulation apparatus. The apparatus includes an electrode array system having at least two (i.e., two, three, four, or more) electrodes; and a conduit interconnecting the electrodes. The conduit contains an electrically conductive fluid in contact with a phase positioned in a pressure chamber. The phase can be, for example, a binding medium or stationary phase.

45 Claims, 8 Drawing Sheets

PRESSURE-ENHANCED EXTRACTION AND PURIFICATION

CROSS-REFERENCE TO RELATED APPLICATION

This application is a continuation-in-part of U.S. Ser. No. 08/962,280, filed on Oct. 31, 1997, now U.S. Pat. No. 6,111,096, which is hereby incorporated by reference.

FIELD OF THE INVENTION

The invention is in the general field of methods and devices for isolating and purifying compounds from mixtures.

BACKGROUND OF THE INVENTION

Many methods for separating biomolecules from mixtures such as cell lysates or synthetic preparations are based on a procedure in which the sample is loaded onto a column packed with a solid phase.

In the case of nucleic acids, for example, the solid phase can include an anion-exchange medium or resin. The negatively charged, anionic phosphate backbone of a nucleic acid can bind to and is thereby effectively immobilized by the resin. The resin can be washed with a low salt solution (e.g., 0.2 M sodium chloride), which flushes away the neutral, cationic, and less highly charged anionic components of the original mixture without substantially disrupting the binding of the nucleic acid molecules to the solid phase.

A high salt buffer solution (e.g., a buffer containing 1 M sodium chloride) is then used to elute the nucleic acid molecules away from the solid phase. The high salt concentration, however, can interfere with mass spectroscopy, electrophoresis, and many downstream enzymatic processes commonly employed in the laboratory or clinic, for example, for diagnostics, forensics, or genomic analysis. It is therefore necessary, in many cases, to remove at least some of the salt from the nucleic acid in an additional, frequently time-consuming step. Desalting can be accomplished by any of several procedures, including ethanol precipitation, dialysis, and purification from glass or silica beads or resin. In some cases it may also be necessary to add nuclease inhibitors to the wash and buffer solutions to prevent degradation of the nucleic acid.

SUMMARY OF THE INVENTION

The invention is based on the discovery that hyperbaric, hydrostatic pressure reversibly alters the partitioning of biomolecules between certain adsorbed and solvated phases relative to partitioning at ambient pressure. The new methods and devices disclosed herein make use of this discovery for highly selective and efficient, low salt isolation and purification of nucleic acids from a broad range of sample types, including forensic samples, blood and other body fluids, and cultured cells.

In one embodiment, the invention features a pressure-modulation apparatus. The apparatus includes an electrode array system having at least two (i.e., two, three, four, or more) electrodes; and a conduit interconnecting the electrodes. The conduit contains an electrically conductive fluid in contact with a phase positioned in a pressure chamber. The phase can be, for example, a binding medium or stationary phase. It can be a gel (e.g., a pressure-sensitive gel), a resin (e.g., an ion-exchange resin, a hydrophobic resin, a reversed phase resin, or a size exclusion resin), a plastic, a glass, hydroxyapatite, an immobilized oligonucleotide, a silica, an ion-exchange material, silicon or other metal, an alumina, a zeolite, a cellulose, a particle, a microparticle, a nanoparticle, a coating on a substrate, a soluble polymer, a micelle, a liposome, a porous solid medium, a membrane, a pressure-stable medium (e.g., DEAE-coated glass, quartz, thermoplastic polymer, gel, or a non-porous resin made up of 1 to 50 $\mu$m beads with positively charged surface), or a phase of a phase-separated liquid. The electrodes can have a protective coating (e.g., of polyacrylamide gel.

The apparatus can also include at least one (i.e., one, two, three, four, or more) reservoir in communication with the conduit to contain materials transported by the conduit. The reservoir can also be positioned in the pressure chamber. The conduit can be, for example, an electrically non-conducting tube. The apparatus can also include a pressure-transmitting apparatus (e.g., an electrically mediated pressure actuator, such as an electrostrictive apparatus, magnetostrictive apparatus, or a shape-memory alloy device) that can transmit pressure to or from the pressure chamber. If there are three electrodes or more, the electrodes can be configured in a straight line or can alternatively define two or more (i.e., two, three, four, or more) axes. The conduit can include an electrophoretic or electroosmotic capillary. The electrode array system can be configured on a microchip.

The invention also features a method for purifying nucleic acids from a sample. The method includes the steps of contacting the sample with the phase of the aforementioned apparatuses at an initial pressure (i.e., where the phase is a phase that non-specifically binds to nucleic acids with greater affinity than it does to non-nucleic acid components of the sample); transporting (e.g., electrophoretically or electroosmotically) at least some of the non-nucleic acid components (e.g., towards one electrode, or away from the nucleic acids); modifying the pressure to a level sufficient to disrupt the binding of the nucleic acids to the phase; and transporting (e.g., electrophoretically or electroosmotically) the nucleic acids (e.g., towards a second electrode, or away from the phase).

In another embodiment, the invention features another method for isolating and purifying nucleic acids from a sample. The method includes the steps of applying the sample to a phase at an initial pressure (i.e., where the phase non-specifically binds to nucleic acids with greater affinity than it does to non-nucleic acid components of the sample); spatially separating (e.g., by electrophoresis, electroosmosis, or fluid flow) at least some of the non-nucleic acid components from the phase and the nucleic acids; modifying the pressure to a level sufficient to disrupt the binding of at least some of the nucleic acids to the phase; and spatially separating the nucleic acids from the phase at the modified pressure. The "applying" and first "spatially separating" steps, at least, are carried out within a single reaction vessel (e.g., a pressure modulation apparatus, or a pressurized vessel).

The first "spatially separating" step can include transporting the non-nucleic acid components into a reservoir. The reservoir can optionally include binding materials such as ion-exchange materials, desalting (mixed ion-exchange) resin, nonspecific affinity resin, polystyrene resin, gamma-irradiated polystyrene resin, a covalent attachment resin (e.g., an aldehyde-rich surface, a carbodiimide-rich surface, an o-methylisourea-rich surface, an amidine-rich surface, a dicarbonyl-rich surface, a hydrazide-rich surface, or a thiol-rich surface), a resin or combination of resins possessing different binding functionalities, or a hydrophobic material; alternatively, an anion-exchange material can be placed at one or more electrodes of positive potential or a cation-exchange material can be placed at one or more electrodes of negative potential.

The initial pressure can be, for example, ambient pressure and the modified pressure can be an elevated pressure (e.g., 100 to 200,000 psi, 500 to 100,000 psi, 1,000 to 50,000 psi, or 2,000 to 25,000 psi).

In some instances, the sample can include cells; the method would then also include subjecting the sample to a hyperbaric pressure sufficient to lyse the cells. The cells can include both external and nuclear membranes, and the hyperbaric pressure can be sufficient to lyse both membranes, or alternatively, only to lyse the external membrane, not the nuclear membranes.

The sample can also include nucleic acid-binding proteins (e.g., nuclease enzymes); the method can thus also include subjecting the sample to a hyperbaric pressure sufficient to inactivate the nucleic acid-binding proteins.

The sample can include various sizes of nucleic acids; the modified pressure level can, for example, be sufficient only to disrupt the binding of relatively small nucleic acids to the phase. To disrupt the binding of larger nucleic acids, and the method also includes the steps of further modifying the pressure to a level sufficient to disrupt the binding of the relatively larger nucleic acids to the phase; and spatially separating the nucleic acids from the phase at the further modified pressure. By this method, for example, a 250 base pair nucleic acid can be separated from a 500 base pair nucleic acid, a 1000 base pair nucleic acid can be separated from a 2000 base pair nucleic acid, or a 10,000 base pair nucleic acid can be separated from a 20,000 base pair nucleic acid.

The sample can be, for example, a biological fluid, whole blood, serum, plasma, cultured cells, tumor biopsy tissue, plant tissue, or living tissue (e.g., tissue in which most normally processes associated with life are ongoing; can be from a living or deceased organism).

The nucleic acids can be partially digested, and fragments of a particular size distribution can be recovered (e.g., for use in sequencing or hybridization analysis). The nucleic acids can include RNA (e.g., total RNA, messenger RNA (mRNA), viral RNA, ribosomal RNA (rRNA)) or DNA (e.g., chromosomal DNA, a vector, or viral DNA).

The modified pressure can be sufficient to elute vector DNA (e.g., typically around 5,000 to 20,000 base pairs, regardless of source; it can include, e.g., digested chromosomal DNA) but not high enough to elute chromosomal DNA (e.g., typically 50,000 base pairs or more). This method would require pressures in the range of, for example, 15000 to 30000 psi, depending on the nature of the phase, temperature, pH, ion concentration, etc.

Similarly, the modified pressure can be sufficient to elute RNA but not high enough to elute chromosomal DNA (e.g., 10,000 to 30,000 psi, depending on phase and other conditions).

A dicarbonyl compound can also be added to the sample to inactivate nucleic-acid binding proteins such as nucleases. Pressure can, for example, accelerate the condensation of guanido moieties, such as arginine residues within the proteins, with the dicarbonyls.

In some cases, the nucleic acids can be concentrated (e.g., at an elevated pressure) between two membranes by electrophoresis, wherein one of said membranes is substantially impermeable to nucleic acids and the second membrane has increased permeability to nucleic acids under applied electrical potential. In another case, the nucleic acids can be trapped in a filter by electrophoresis.

The nucleic acids can be transported to an analytical device (e.g., a matrix-assisted laser desorption and ionization (MALDI) mass spectrometer).

The invention also features a device for carrying out the aforementioned methods. The device includes a pressure modulation apparatus; and a pressurizable cell containing the phase. The cell is adapted to fit within the apparatus.

In still another embodiment, the invention features a device for pressurizing a sample. The device includes a sample compartment; and a pressure-transmitting apparatus to transmit pressure from a pressurizing medium outside of the device to the sample compartment, without allowing fluid flow between the medium and the sample compartment.

The device can also include a chamber having an orifice, wherein the sample compartment and the pressure-transmitting apparatus are configured within the orifice. The pressure-transmitting device can include, for example, a shape-memory alloy device, or a magnetostrictive device. The chamber can be in the form of a cylinder (e.g., a plastic tube with one sealed end and one open end) and the pressure-transmitting apparatus can be a piston (e.g., a rubber piston, or a syringe plunger). The chamber can alternatively be a well in a microtiter plate. The invention also features a method for permeabilizing (or lysing) cells. The method includes the steps of charging the sample compartment of the preceding device with cells at an initial pressure; introducing the device into a pressure modulation apparatus; and momentarily increasing the pressure to at least 10,000 psi to permeabilize the cells. The cells can be, for example, yeast, bacteria, animal, or plant; the initial pressure can be less than, equal to, or greater than atmospheric pressure; the permeabilized cells can be removed and electrophoresed, or purified electrically (e.g., electrophoretic washing or washing with fluid driven by electroosmotic flow); a detergent can be added to the cells prior to or after pressure treatment. The sample compartment can also be charged with a gas (e.g., air). Additionally, a voltage can be applied across the sample compartment to spatially separate at least some components of the permeabilized cells from other components of the cells. The cells can additionally be frozen.

Yet another embodiment of the invention is the use of hyperbaric pressure to modulate binding affinities associated with an ion-exchange material (e.g., an anion-exchange resin, or a cation-exchange resin) for use in ion-exchange chromatography. This can include traditional or capillary chromatography, and the chromatographic substrates can include nucleic acids, proteins, carbohydrates, or other small molecules. The method can be also be integrated with lysis or electrophoresis methods.

Another embodiment of the invention is a method for the isolation of molecules from cells. The method includes the steps of exposing the cells to an elevated pressure of at least 500 psi (e.g., 1,000, 2,000, 5,000, 10,000, 20,000; 30,000, 50,000, or 100,000 psi, or even higher) in a pressure chamber to form lysed cells; and separating the molecules from the cells within the pressure chamber. The method can be carried out in an integrated device (e.g., a consumable, single-use cartridge). The pressure can be pulsed or cycled between the elevated pressure and ambient pressure at least twice (e.g., two, three, four, or more times) The cells can be, for example, yeast, bacteria, fungi, animal cells, plant cells, insect cells, or protozoan cells.

The molecules can be extracted by elution with a flowing solvent, electrophoresis, electroosmosis, selective absorption to an absorptive medium, filtration, differential sedimentation, volatilization, distillation, gas chromatography, or precipitation. The molecules can be extracted while the cells are at the elevated pressure. The pressure can be raised to its final value in less than 1 second (e.g., less than 0.1 second). The method can also include the step of returning the cells to ambient pressure, for example, in 1 second or less (e.g., 0.1 second or less). The molecules can be purified, at least partially, within the integrated device.

The molecules can also be purified by elution with a flowing solvent, electrophoresis, electroosmosis, selective absorption to an absorptive medium, filtration, differential sedimentation, volatilization, distillation, gas chromatography, or precipitation. The purifying step can, for example, requires a change in pressure of at least 500 psi.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety In case of conflict, the present application, including definitions, will control. In addition, the materials, methods, and examples are illustrative only and not intended to be limiting.

An important advantage of the new methods is the potential for use of a single solvent for both isolation and purification of nucleic acids. A single solvent can be used for 1) loading the nucleic acid-containing sample onto the immobilized solid phase, 2) washing non-nucleic acid impurities away from the immobilized nucleic acid, and 3) dissociating the nucleic acid from the solid phase. Additionally, if the sample includes cells, the cells can be lysed by hyperbaric pressure in the same solvent as is used for loading, washing, and dissociating.

A single solvent method can be more cost-efficient, can generate less waste, and is generally simpler to implement. Furthermore, the solvent can be the same buffer that is used for a downstream reaction. For example, prepackaged buffers, such as those containing magnesium salts and other cofactors for use in the polymerase chain reaction (PCR), can be used as the loading, washing, and elution buffer in the new methods.

The use of a single, low-salt solution enables electrophoresis of biomolecules through an ion-exchange matrix, at a pressure that allows the desired molecules to adhere to the solid phase, while undesired molecules are removed by electrophoresis to a waste reservoir. The pressure can then be modulated to release the desired molecules, which can be collected by further application of an electric field. This method is compatible with miniaturized "blochip" devices which can utilize methods of high-volume manufacturing.

Another advantage of the new methods is the use of solvents that minimize damage to biomolecular constituents. Because pressure can be used to assist the lysis of the cells (if any) in the sample, there is no need for harsh lysis solutions (e.g., phenol/chloroform, guanidinium salts, chaotropic salts) that are often used in vast excess and must subsequently be removed. Since pressure can also be used to reduce the affinity of the biomolecules for the solid phase, high-salt elution solvents are not necessary.

Pressure can also be used to selectively lyse, for example, the cell wall or external membrane without lysing the nuclear membrane. This can be useful for isolation of vector DNA, for example, from the cytoplasm, while leaving chromosomal DNA (i.e., in the nucleus) behind.

Yet another advantage ensues from the obviation of the need for high-salt elution solvents: the need for desalting procedures is avoided. Desalting is generally necessary if, for example, the purified nucleic acids are to be used in further reactions or processes such as PCR, transfection, transformation, electroporation, electrophoresis, mass spectroscopy, quantification with fluorescent dyes, in vitro translation, stringent hybridization, sequencing, genetic engineering, ligation, restriction digestion, genomic mapping, clinical diagnostics, or hybridization with other molecules. In the present methods, the eluted biomolecule-containing solution does not need to be desalted. The new methods also do not require precipitation in organic solvents, or binding of the nucleic acids to silicon or glass beads for desalting.

The use of low salt buffers also allows the new methods to be compatible with electrophoretic or electroosmotic transfer of materials. Salt can cause excessive heat generation in these processes. Electrophoretic devices are generally inexpensive, can be incorporated into other devices, and can allow isolation of, for example, less fragmented nucleic acids (e.g., compared to flow techniques). Electrophoresis can also be used to concentrate nucleic acid samples (i.e., electroconcentration).

Still another advantage of the present methods is that the methods avoid the need for addition of nuclease inhibitors. The majority of proteins are believed to be denatured at pressures lower than 100,000 psi at ambient temperature and neutral pH, whereas nucleic acids can withstand substantially higher pressures. Altering pH or temperature can further enhance protein denaturation. Thus, a pressure pulse of, for example, 120,000 psi at pH 4 and 25° C. can effectively inactivate nuclease activity without adversely affecting the desired nucleic acids.

Moreover, it is known that arginine residues of proteins react with 1,2 and 1,3-dicarbonyl compounds such as phenyl glyoxal, 2,3-butanedione and 1,2-cyclohexanedione, to form condensation products that can be stabilized by borate ions (Creighton, TE, "Proteins: Structures and Molecular Properties, 1993, W.H. Freeman and Company: New York, pp 12–13 and references therein). By using a dicarbonyl compound that is attached to a solid support, nucleic acid binding proteins such as nucleases and histones may be retained in the purification process. A charged molecule bearing a dicarbonyl moiety is useful since excess reagent can be removed by electrophoresis. The condensation of arginine with a dicarbonyl compound can be accelerated by pressure.

Centrifugation is generally avoided in the processing of the samples for the new methods. This is an advantage in that centrifugation can generate shearing forces and pressure drops that may irreparably damage the integrity of many biomolecules, thereby decreasing the yield and quality of the isolation. Moreover, the new methods eliminate much of the handling and pipetting of the biomolecule-containing solutions. As a result, much longer mRNA strands, for example, which can be shorn by routine handling and pipetting, can be isolated intact, thereby facilitating formation of more reliable cDNA libraries, even from mRNA molecules present in low concentration or low copy number. The new methods can give yields of greater than 95% with high purity and speed.

Because all of the steps in the new methods can be carried out in a single solvent, no additional time is required for manipulation of solvents prior to each step. Moreover, the effects of pressure are manifest very rapidly; pressure is transferred through the sample at the speed of sound. As a result, the new methods require only the time that it takes to spatially separate the sample constituents; the need to wait for the nucleic acid to precipitate in alcohol, for example, is avoided.

Furthermore, the new methods can be scaled up or down over a large range of sample sizes, from the isolation of the genomic DNA from a single hair follicle to the purification of a plasmid from a megaprep of bacteria. Sample volumes as small as 1 femtoliter or as large as 5 liters (e.g., for commercial nucleic acid preparation) can be accommodated by the new methods. Small-scale nucleic acid isolations can be completed within seconds; large-scale isolations may take a few minutes.

Moreover, essentially the same methods can be used for the isolation of small nucleic acids (e.g., less than 50 bp) or large nucleic acids (e.g., larger than 1,000,000 bp). The small molecules elute at lower pressures and lower salt concentrations, and can therefore be independently isolated from samples containing both large and small nucleic acids.

The new methods are also suitable for isolating nucleic acid from a broad range of samples, including, but not limited to, blood, urine, semen, mucal scrapings, sweat, hair, bone, pus, saliva, fecal matter, biopsy tissue, amniotic fluid, synovial fluid, plasma, prokaryotic (e.g., bacteria) or eukaryotic cultures (e.g., plant tissue, yeast, tumor cells), viruses, viroids, and blood-stained materials. Pressure can also enhance dissociation of proteins from nucleic acids.

Hyperbaric pressure can cause nucleic acids to adopt compact configurations which confer added resistance to shearing, nicking, and enzymatic degradation, thus yielding a purified nucleic acid of improved quality.

The use of hyperbaric pressure also improves electrophoretic and electroosmotic processes by suppression of gas bubble formation, which can block the transmission of electric fields.

The new methods are also amenable to automation The new methods require little human intervention; no additional pipetting, decanting, centrifugation, precipitation, or resuspension of the nucleic acid is generally required. The methods are also highly efficient, and are thus both cost-effective and suitable for high-throughput screening processes (e.g., genetic screening, drug screening). Since the new methods rely on physical processes, little customization is required for different applications (i.e., sample specimens).

In an example of high-throughput methods, a multicolumn array is used. Such an array can include ninety-six miniature columns built into a microtiter plate-type device, each column packed with DEAE cellulose retained by a frit and having a volume of a few hundred microliters. In another version, the array can include patches of a NUCLEPORE®-type (Corning Separations Division, Acton, Mass.) track etch membrane, derivatized to include charged groups. Each individual pore would effectively be a "column" of ion-exchange material, with a volume of about a femtoliter each. Several thousand of these columns can be present in each patch. The separation material and the wall of the column can be made of the same substance. In still another version, separation columns can be microfabricated on chips measuring only a few microns in lateral dimension. Such columns can either contain a filling material or use the walls of the device as a separation material.

Typical procedures for RNA purification require lysis using chaotropic agents (e.g., guanidinium salts, sodium dodecyl sulfate, sarcosyl, urea, phenol, or chloroform), which disrupt the plasma membrane and subcellular organelles, and inactivate ribonucleases, or using a gentler solution that only solubilizes the plasma membrane (e.g., hypotonic nonidet P-40 lysis buffer). The latter reagents also require addition of a nuclease inhibitor. Organic solvent extraction or silica membrane absorption methods are then be used to extract the RNA from the cell lysate. Using the new pressure-based methods, however, cell lysis and RNA purification can be combined in a single procedure. This offers the advantages of reduced human intervention, better control of contamination with RNase, and a rapid processing speed, which also reduced the potential for RNA degradation.

Other features and advantages of the invention will be apparent from the following detailed description, and from the claims

DETAILED DESCRIPTION OF THE INVENTION

Figure 1:
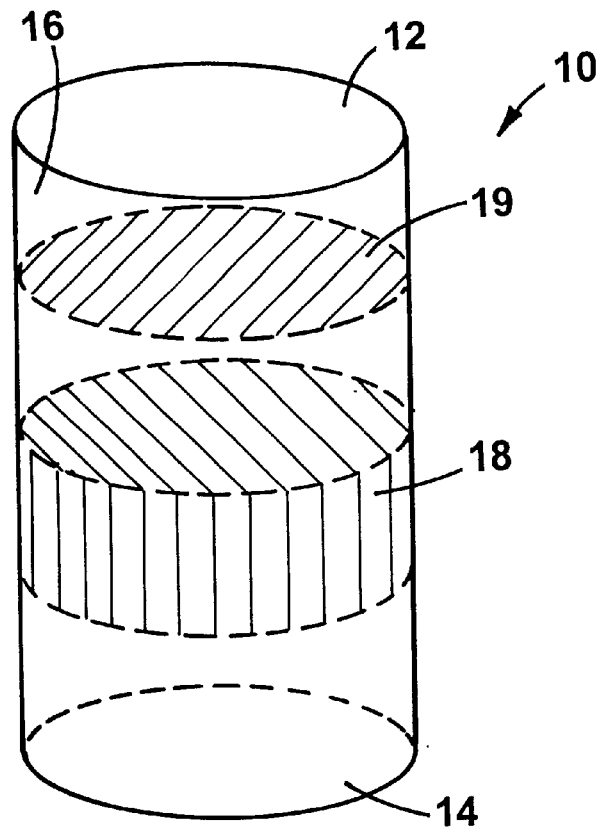
FIG. 1 is a drawing of a resin-filled cartridge for use in a pressure-modulation apparatus.

Methods and devices are described for the highly selective and efficient, low ionic strength isolation and purification of biomolecules (e.g., nucleic acids, proteins, carbohydrates, and small molecules) from many types of samples. The invention is based on the observation that pressure can be used to effect the dissociation of nucleic acids and other biomolecules from solid phases to which they normally bind tightly (e.g., anion-exchange resins), even at low salt concentrations.

General Procedure

In general, a solution containing a biomolecule to be purified is introduced onto a solid phase at low pressure (e.g., ambient pressure). The solid phase, to which the biomolecule present in the solution should now be bound, is washed with a buffered second solution, in which the desired biomolecule will remain bound to the solid phase at elevated pressure, whereas the undesirable contaminants (e.g., proteins and lipids) will be removed from the solid phase. When the washing has been completed, the pressure is increased further to a level sufficient to cause the desired biomolecule to be freed from the solid phase. While this elevated pressure is maintained, fresh low salt buffer can be used to wash the liberated biomolecule away from the solid phase and into a collection vessel. These procedures can be fully automated. The recovered biomolecule is free from high salt and can be used in downstream enzymatic reactions.

Biomolecules that can be purified by this procedure include nucleic acids (e.g., chromosomal DNA, viral DNA, plasmid DNA, mitochondrial DNA, a DNA vector, an oligonucleotide, mRNA, mitochondrial RNA, viral RNA, or mixtures of nucleic acids), proteins (e.g., enzymes, antibodies, structural proteins, metalloproteins, hormones, glycoproteins, mucins), and carbohydrates and other small molecules (e.g., sugars, dyes, synthetic drugs, cofactors, amino acids). The solid phase can be made from any substance that selectively binds the desired biomolecule at ambient pressure and has reduced affinity at elevated pressure, such as an anion-exchange column, an oligo-dT column, or an electrode coated with absorptive polymers.

In addition to binding to the desired biomolecule, the solid phase can have other functions. For example, the solid phase can absorb the biological samples (e.g., a sponge-type polymer); it can assist in the lysis of the cells, for example, by mixing the solid phase material with proteases (e.g., pepsin or trypsin), lipases, or glycosidases (e.g., lysozyme) to digest proteins, lipids, and polysaccharides, respectively; or it can include DNase for RNA purifications, or RNase for DNA purification. Some solid phases can bind nucleic acids, but only weakly interact with other negatively charged molecules such as some proteins or lipids, or vice versa.

The same solution or different solutions can be used to load the biomolecule sample onto the solid phase, elute the impurities away, and elute the biomolecule away from the solid phase. Nonetheless, it is generally most desirable to use a single buffer, both for ease of operation and to reduce waste. Whether the solution acts as a wash buffer or as an elution buffer depends on the pressure. At pressures greater than about 25,000 psi, for example, large nucleic acids (e.g., more than 5,000 bp) can be eluted in low salt buffers. In addition, at 25,000 psi, small nucleic acids such as those used in the Sanger sequencing method can be eluted at still lower salt concentrations. At ambient pressure, however, it is necessary to use an eluent having a much higher concentration of salt. High salt eluents can interfere with downstream reactions, especially enzymatic reactions used in the manipulation of nucleic acids (e.g., for sequencing or amplification), and are therefore ideally avoided.

As described above, for a low salt buffer to be an effective elution solvent, the pressure in the vicinity of the solid phase must be greatly increased, often to several thousand times ambient pressure. Suitable pressure-modulation apparatuses for generating the requisite pressure are described at pages 4–9 and 29–44 and in FIGS. 1 and 4 of PCT Appln. No. US/96/03232, which is given Ser. No. 08/793,213 in the U.S. National Phase and issued on Mar. 14, 2000 as U.S. Pat. No. 6,036,923, and is hereby incorporated by reference. A chip or a cartridge containing the solid phase can be inserted into this apparatus, for example, and the purification can be carried out within the apparatus. The apparatus can be made in various configurations to accommodate the full range of sample sizes.

Other properties important to separation can also be altered by pressure. These include the denaturation and refolding of proteins and the association of nucleic acids into double-stranded forms (or dissociation into single-stranded forms), both of which can affect the filtration, sedimentation velocity or equilibrium, radius of gyration, exclusion volume, electrophoretic mobility, and/or chemical reactivity of biomolecules. Any of the separation techniques described herein can be used to equivalent effect by selection of appropriate conditions.

All of the steps of biomolecule purification, including lysis, binding, elution, and isolation, can be automated. Additionally, the pressure can be scaled up to allow elution of progressively larger biomolecules, thereby facilitating the isolation of specific sizes of molecules. A pressure gradient (i.e., either stepped or continuous) can also be set up within the devices. A pressure gradient (e.g., step function) can be used, for example, to fractionate samples. Fractionation can be used to purify specific fragments from a partially degraded sample or a highly diverse sample (e.g., a cDNA library).

Pressure can alter the effective hydrodynamic radius of gyration of a macromolecule such as a nucleic acid or a protein. In general, such a change can alter the elution position (i.e., $V_e$, the exclusion volume) of the macromolecule on a size-exclusion medium (e.g., silica, a rigid plastic such as polystyrene, or a porous hydrogel such as SEPHADEX™ and SEPHAROSE™ (Pharmacia) resins). The molecule does not need to bind to the resin; rather, the molecule's ability to enter a pore can be affected by the hydrostatic pressure at which the separation is conducted. The ability to select a pore size such that a given molecule is included at one pressure and excluded at another can allow improved separations. In particular, molecules that co-elute at one pressure can be separated at another.

Nucleic Acids

Examples of applications of the present method include purification of nucleic acids from blood, cell culture (genomics or infectious disease) or tissue (e.g., tumor biopsy) for clinical or research purposes, purification of microbial DNA for genetic or biotechnology research, desalting of DNA, forensic analysis (e.g., purification of DNA from hair, blood, semen, or tissue found at the scene of a crime), and purification of PCR products.

The isolation and purification techniques of the invention can be applied to both natural and artificial nucleic acids. Artificial nucleic acids are typically based on ribose or deoxyribose, or geometrical analogs thereof. Linkages other than the natural phosphodiester bonds can be employed in artificial nucleic acids, including thiophosphate and amide bonds.

Among RNA molecules, the most common classes include mRNA (messenger RNA), tRNA (transfer RNA), rRNA (ribosomal RNA), viral RNA, and RNA that has been copied from DNA in vitro.

For most applications, chromosomal DNA is linearized from a cyclic form, if present as such, and can also broken into smaller pieces for ease of manipulation. The breaking may be done non-specifically (e.g., using the exonuclease DNase I, or by sonication); or by specific cutting with an enzyme (a "restriction endonuclease") or by chemical means; helicases, topoisomerases, kinases, and other nucleic acidspecific enzymes can also be used, for example, to alter migration or absorption properties of the nucleic acids. If no other alterations have been made, such DNA may still be generally referred to as chromosomal.

A plasmid is an independently replicating DNA found in bacteria, generally circular, and is often used for transmission of genes in biotechnology. Plasmid DNA may also be cut into small pieces, usually by restriction enzymes. The fragments produced by restriction enzymes are often named by their apparent molecular weights, in "base pairs" or "bases" of DNA. For example, a "4.6 kB" DNA fragment is about 4,600 bases long, whether it is double stranded or single stranded.

Most proteins (e.g., nucleases) are inhibited bv pressure. A 120,000 psi pulse, for example, can irreversibly denature the nucleases in a sample. It is important, especially in attempted isolations of RNA, to denature nucleases such as RNAse to prevent degradation of the desired nucleic acids during the isolation process. Pressure can be used here in place of chemical inhibitors. In some cases, nuclease denaturation and cell lysis can be accomplished simultaneously.

Ribonuclease A is subject to cold-denaturation at elevated pressures. Addition of a reducing agent can subsequently facilitate irreversible denaturation by reducing the disulfide bonds of the nuclease. Thus, for example, 10 mM β-mercaptoethanol can be added to a sample, the sample can be cooled to −20° C., and the pressure can be increased to 60,000 psi to irreversibly denature the nuclease.

Additionally, activation of RNases may be desirable for certain applications, such as for the extraction of genomic DNA. In this case, conditions that activate or enhance RNase activity can be obtained through a combination of temperature, pH, or pressure (e.g., using pressures high enough to accelerate enzymatic activity, but still lower than the pressures required to denature the enzyme).

For example, at 220 MPa (about 32,000 psi), 100% of Lambda DNA (XDNA) was eluted off a DEAE column with 50 mM Tris-HCl buffer, pH 8.5. At atmospheric pressure (0.1 MPa, or 14 psi), higher salt buffers (e.g., 1 M sodium chloride Tris-HCl buffer) are generally required to elute the DNA away from the DEAE resin. Moreover, plasmid DNA dissociated at lower salt concentrations and lower pressures than XDNA. Thus, low molecular weight DNA molecules can be dissociated at lower salt concentrations and lower pressures than higher molecular weight molecules. For sample analysis and other applications, it can be useful to separate nucleic acid fragments by size.

Eukaryotic cells can express cloned genes (i.e., transient and stable heterologous expression), using eukaryotic expression vectors purified by the new methods. To analyze and identify the function of cloned eukaryotic genes, for example, eukaryotic expression plasmids carrying the gene of interest can be obtained in a form suitable for introduction into mammalian cells. It is often necessary to generate a large panel of mutants for structure-function studies of a particular eukaryotic gene. Therefore, the new methods provide a method for rapid and facile analysis.

Isolation of DNA by the new methods can be used for numerous applications including, but not limited to, protein expression and protein structure function studies in eukaryotic cells, Southern blot analysis, in vitro transcription, ligation, and transformation, heterologous protein expression in bacteria or yeast, microinjection studies, PCR, DNA sequencing, viral DNA detection, paternity testing by RFLP analysis, and genetic screening by singlestrand conformation polymorphism (SSCP) or non-isotopic RNase cleavage assay (NIRCA™; Ambion, Austin, Tex.). Similarly, isolation of RNA provides a variety of applications including, but not limited to, genetic analysis, cDNA library construction, microinjection into oocytes, differential display, Northern blot analysis, RNase protection assays, in vitro translation, reverse transcriptase PCR (RT-PCR), and detection of viral RNA (e.g. HIV, hepatitis C, hepatitis A, and HTLV-1) in human blood. Isolation of nucleic acids produced in vivo generally requires the lysis of the host cells in which the nucleic acids are contained. Any cell lysis method can be employed in conjunction with the new methods, provided that it produces a yield and quality of nucleic acid sufficient for an intended subsequent use. Lysis can be carried out inside or outside of a pressurized or pressurizable apparatus.

Cells differ in their resistance to lysis. For example, many animal cells can be lysed through contact with even small amounts of detergents or organic solvents. Animal cells have little or no containing structure except a plasma membrane and its embedded proteins. Dissolution of the cellular membrane allows all of the cellular contents to diffuse into the lysing solution.

Animal cells can also be lysed by changing the osmolarity of the solution (e.g., by lowering it from its normal level of about 300 mOsm to about 0 to 10 mOsm. Osmotic lysis is especially effective on cells which are normally exposed to a fixed, normal osmolarity, such as human tissue.

Animal cells can also be lysed by chemical, enzymatic (e.g., proteases can be used in conjunction with chemicals to lyse membranes when purifying nucleic acids), or mechanical methods. For example, mammalian tissues can be lysed by strong mechanical shear in solution, such as by grinding and dispersing with a Dounce homogenizer or a kitchen blender.

Viruses can generally be lysed under conditions similar to those described above for the lysis of animal cells. Some viruses can be lysed under even milder conditions, such as a change in ionic conditions (e.g., by removal of polyvalent cations) or temperature.

Bacterial cells often have strongly crosslinked cell walls in addition to plasma membranes. Consequently, they can be more difficult to lyse than animal cells. The cell walls are generally resistant to most detergents and chemicals, and also stabilize the plasma membrane against rupture by change in osmolarity. However, bacteria can be grown in the presence of antibiotics (or under specific metabolic conditions) that prevent the formation of cell walls, facilitating subsequent lysis by the means described above in connection with animal and viral cells.

Yeast cells, most plant cells, and some insect cells have still more durable cell walls. More powerful methods are required for lysis of such cells. These methods, which can also be used for lysis of the less robust cell types described above, include sudden depressurization from high pressure to atmospheric pressure, often by flow from a pressurized cell through a fine needle (i.e., French press). An alternative for rupturing the durable cell walls is the grinding of cells with glass beads (or other durable particles), often in a violently reciprocating shaker (e.g., in a "Nossal shaker"). When prevention of enzymatic activity after cell lysis is particularly critical, cells or tissues can be frozen, for example in liquid nitrogen, and then ground in the frozen state ("cryogrinding").

One method for purifying DNA relies on the absorption of DNA by silica at high concentrations of chaotropic salt, especially sodium iodide. Typically, DNA is absorbed to the silica surface at this high salt concentration, and impurities (and excess iodide) are washed away in the presence of methanol/water. On reduction of the methanol concentration, the DNA is released. This process can be pressure-sensitive, and thus either some of the expensive sodium iodide can be replaced by application of the DNA to the silica resin at high pressure, or the elution itself can be facilitated by pressure modulation.

Hyperbaric Cell Lysis and Extraction

For the purification of non-secreted biomolecules from cells (e.g., from cell cultures or tissue), the cells must be lysed, or at least permeabilized, prior to the introduction of the sample onto the solid phase. There are many known methods for cell lysis, as described above in connection with the isolation of nucleic acids, including chemical methods (e.g., phenol/chloroform extraction, treatment with guanidinium salts, chaotropic salts, detergents such as sodium dodecyl sulfate, or enzymes such as proteinase K) and physical methods (e.g., boiling, French pressing, Douncing, vortexing in the presence of glass beads, or sonication—see, e.g., Bollag et al., "Protein Methods," 2nd Ed., 1996, pp. 27–56). Often these methods can be sensitive to variations in time and temperature.

Another suitable method is the use of hyperbaric pressure to cause cell lysis. Hyperbaric lysis can be carried out in the same solvent as will be used as the loading buffer for later introducing the sample onto the solid phase, or can be carried out in a different solvent. Still another suitable method is the use of a chemical agent (e.g., a detergent) in combination with pressure. For example, a small amount of a chaotropic salt can be used to prime the cells for lysis; after the cells have been treated with the chaotropic agent, they can be lysed at lower pressure.

More gentle lysis procedures can be especially preferable for isolating single-strand (e.g., RNA) or high molecular weight nucleic acid molecules. Single strand nucleic acids are more easily shorn; high molecular weight nucleic acids are statistically more likely to be damaged during lysis. Furthermore, pressure-based lysis can be used to preferentially fractionate cellular material (e.g., lysis of external cell wall/membrane while maintaining the nuclear membrane for the isolation of extranuclear constituents).

By modulating hydrostatic pressure, a tissue or cell suspension can be rapidly frozen and thawed while maintaining a low temperature. This technique can be advantageous in that the action of nuclease enzymes can be inhibited at low temperature; nucleases can also be denatured by pressure at low temperature.

In a typical procedure, the sample is cooled to $-20°$ C. to freeze the sample, then the pressure is cycled between 60,000 psi (i.e., to melt the sample) and 14 psi (i.e., to re-freeze the sample) repeatedly until the sample is sufficiently disrupted. Alternatively, the temperature can be modulated by cyclic application of pressure to a sample or a gas-containing pressurizing medium in proximity to the sample. The compression and decompression of the gas either in the sample compartment or in the pressurizing medium modulate the temperature via the Joule-Thompson effect.

Molecules can be extracted from the cell with pressure, allowing direct application of the extracts to the various solid supports. Pressure-based extraction methods are easily integrated with the hyperbaric methods described herein. Exposure of cells to high pressure can cause lysis or permeabilization of cells without any further treatment. For example, bacteria in a solution in a test tube can be exposed to a pressure of 60,000 psi. While the cells are held at such a pressure, molecules can diffuse out of the cells. Even relatively large molecules such as nucleic acid plasmids can diffuse under these conditions. Application of an electric field across a pressurized sample can further increase the extraction efficiency.

Repeated cycling between ambient and elevated pressures can cause rupture of cells. For example, yeast cells exposed to 30,000 psi for 240 cycles were fragmented, releasing at least some of their intracellular contents. This mechanism of fragmentation is different from that used in a French-type pressure cell, where a pressurized solution containing cells is released through a fine orifice. There, the fragmentation generally requires both a sudden pressure drop and high rate of shear in the solution. The new methods require no shear, and are thus gentler to the cells. In at least some cases, the new methods also do not require sudden depressurization.

Because the sample integrity can be maintained during molecule extraction, the new pressure-based extraction methods allow hundreds, thousands, or even more samples to be processed in parallel. The samples can be in the wells of microtiter plates, for example. For smaller volumes, the cells can be present in droplets on bibulous media. Imprinted boundaries of hydrophobic materials can also be used to separate the droplets. The bibulous material can also serve as the separation medium, binding the desired molecules for later elution. The permeabilizing (or lysis) and separation steps can each be carried out at a high, but isostatic, pressure. Thus, multilayer arrays of bibulous and separation media can be made, having multiple sample spots. Moreover, because the pressure is isostatic, fluids can be processed through such arrays at high pressure without requiring that the array, for example, or machinery handling it within the hyperbaric volume, have sufficient integrity to withstand the pressure differentials. Thus, for example, cells contained in a moist DEAE grid on a paper strip can be pressure-lysed in situ and then "blotted" (wet layer applied "above", dry layer "below") to transfer the molecules of interest to one layer, while the cell debris and extraneous molecules are left behind or transferred to other layers. With suitable equipment, selective extraction and purification of molecules from cells can be substantially automated.

Cells can be lysed in a device intended to carry absorbed biomolecules into a pressure chamber, either before or after application of pressure. The cell debris can be retained by filtration on a medium (e.g., filter paper), while the soluble components (i.e., including the biomolecules) are carried to an absorptive material by pressure-induced flow of buffer. The biomolecules can be later released from the resin by changes in pressure. If further purification is desired, the output of pressure-released biomolecules from the retention medium can be absorbed by another medium (e.g., another resin).

Provision can be made for control of such parameters as shear forces and enzymatic attack on the nucleic acids to be isolated. If, for example, the biomolecule of interest is a small, double-stranded DNA molecule (e.g., a plasmid, a cosmid, or viral DNA) from a bacterium, then it may not be necessary to completely lyse the bacteria. Lysis of the plasma membrane, accompanied by physical and/or chemical treatment (e.g., heating in the presence of protease K) to inactivate DNA-degrading enzymes, can be used to leave the contaminating bacterial chromosomal DNA inside the bacterial cell wall for ease of isolation.

Cartridges

One design for an isolation device is shown in FIG. 1. This device is a cartridge 10 made of metal (e.g., titanium, stainless steel, or aluminum), plastic (e.g., a thermoplastic such as polypropylene or polytetrafluoroethylene), glass, quartz, stone (e.g., sapphire), or a ceramic, adapted to fit into a pressure-modulation apparatus such as those described at pages 4–9 and 29–44 and in FIGS. 1 and 4 of PCT Appln. No. US/96/03232, which was given Ser. No. 08/793,213.

The cartridge is generally formed in the shape of a tubular column, although other designs can be used. Regardless of the shape, the cartridge usually has two openings 12 and 14, one 12 to allow fluid to enter and another 14 to allow the fluid to exit. Between the two openings, but within a channel 16 common to the openings, a solid phase material 18 is packed. The solid phase can be any of a multitude of nucleic acid-binding materials; including silica gel, glass, anion-exchange resin (e.g., DEAE), tethered specific binding molecules. Binding groups, bound to the resin by suitable chemical or physical linkage, can include nucleotides or nucleic acids, tethered proteins or peptides, polymers, DNA-binding molecules (e.g., ethidium, acridinium), or other small molecules (e.g., sugars, benzodiazepines, drugs). The solid phase should ideally be able to withstand the hyperbaric pressures utilized in the new methods without permanent deformation or malfunction. Thus, solid phases that can withstand higher pressures can be preferable (e.g., DEAE-coated glass can advantageously be used in place of certain silica-based resins for some applications).

The cartridge can be designed such that the openings are in direct fluid contact with the reaction chamber of the pressure-modulation apparatus, or can be designed as a closed system with valves and pistons that can open and close to regulate the pressure and the fluid flow within the cartridge. The valves and pistons in this embodiment can be controlled either electronically or mechanically.

Cartridges designed for use with samples derived from lysed whole cells can optionally include a filter or membrane 19, having a pore size suitable for removal of any remaining cell debris prior to introduction of the sample onto the solid phase. This filter may be larger in cross-sectional area than the resin chamber to prevent pressure gradients.

The volume of the cartridges can vary widely. For example, the cartridge can have an internal volume that can range from a femtoliter (fl) up to 10 ml or more (e.g., 1 $\mu$l to 1 ml). A fl is the approximate volume of a 10 $\mu$m diameter capillary penetrating a 100 $\mu$m thick (4 mil) membrane. The volume of the separation medium will depend upon the intended use. Typically, the solid phase occupies about half of the internal volume of the cartridge, although some cartridges can be filled to nearly to their full capacity while others may be filled just one tenth of the way. In some cases, the cartridges can be reused. The volume applied to the column to load it is arbitrary, and the relevant column parameter for separation is the binding capacity of the column.

In an example of one mode of operation of the cartridges, the sample is typically dissolved or suspended in a low-salt buffer solution and introduced at opening 12. The cartridge 10 is placed in the pressure-modulation apparatus. A low pressure flow of buffer solution is used to force the sample through the membrane 19 and through the solid phase 18. Nucleic acids in the sample bind to the solid phase; the flow-through continues through the solid phase and emerges from opening 14. In some cases, the flowthrough is taken up by a sample output tube leading to an input on a detection device (e.g., a UV-vis spectrophotometer). The low pressure flow of the buffer solution is continued until the detection device shows that no additional residues are washed away. The flow-through is discarded.

The pressure is then increased to 500 to 100,000 psi, causing the nucleic acid to be released from the solid phase. More of the buffer solution is introduced through opening 12, and the nucleic acid-containing flow-through that emerges from opening 14 is collected. This flow-through can also be fed into a detection device and analyzed, and the flow continued until the nucleic acid detected in the flow-through falls below a set threshold level.

The cartridges can also include multiple compartments. For example, the individual compartments can contain different solid phase materials (e.g., ion-exchange resin, silica gel, tethered oligonucleotides). Reactions can be carried out within the cartridges.

For instance, a cartridge of the present invention can be used as a PCR reaction vessel, if placed within a thermal cycling apparatus after the solid phase has been washed to remove non-nucleic acid impurities and the nucleic acid has been eluted from the solid phase into, for example, a second compartment in the cartridge.

A multi-compartment cartridge can also be used to concentrate nucleic acids. In such a cartridge, fluids can be moved hydrodynamically or electrically, or both. In one example, DNA from a large sample can be concentrated hydrodynamically onto a resin, small molecule impurities can be washed away, then the DNA can be electrophoresed into a downstream cartridge. This process is herein termed electroconcentration.

In another two-part cartridge, nucleic acids are eluted from a first compartment (e.g., containing an anion exchange resin), using pressure, and concentrated in a second compartment (e.g., containing silica gel) that requires different conditions for elution. Thus, concentrated nucleic acids can be isolated from eve dilute samples containing many impurities. Alternatively, the eluted sample can be automatically transferred to another device (e.g., a disk, a pad, a bead, or a detection device).

Silica and glass are commonly used in isolation of nucleic acids, particularly double-stranded DNA (dsDNA). In a high concentration of a chaotropic salt, such as NaI (sodium iodide), DNA binds to glass surfaces. After other impurities are washed away by a solvent which retains the DNA on the glass, which solution can be the chaotropic salt solution, or an aqueous solution containing a nonsolvent for DNA, such as an alcohol, then the DNA can be released and eluted by exposure of the column to dilute buffer. There are several steps in this procedure in which high pressure might be used to simplify the procedure.

Cartridges containing multiple, layered resins are also within the scope of the claims. A layer of cation-exchange resin, for instance, will capture any positively charged proteins which might bind to the DNA. Hydrophobic (e.g., reverse-phase) resins can bind to the lipids in the sample.

Devices Using Electrophoresis or Electroosmosis

Figure 2:
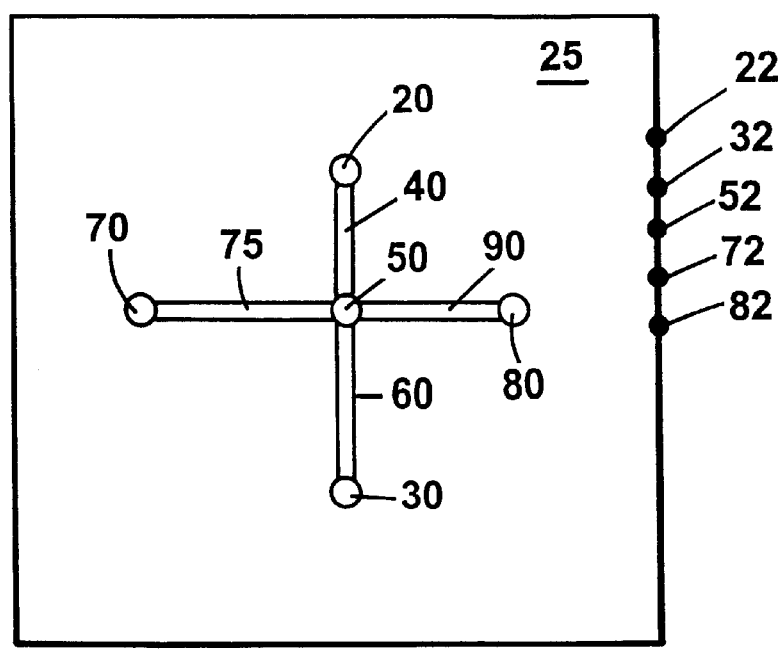
FIG. 2 is a drawing of a five electrode chip for use in a pressure-modulation apparatus.
Figure 3:
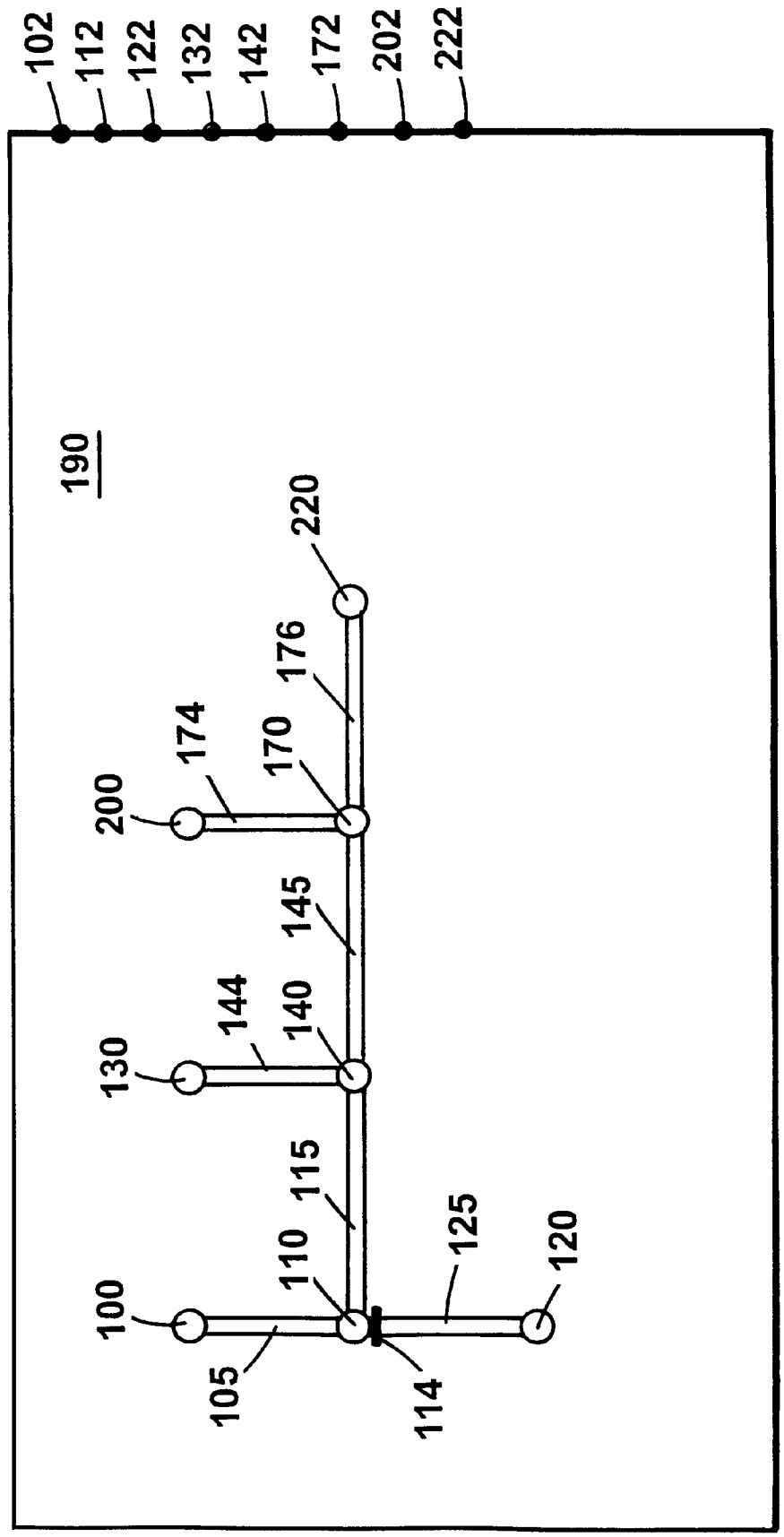
FIG. 3 is a drawing of an eight electrode chip for use in a pressure-modulation apparatus.

Alternative designs for isolation devices are depicted in FIGS. 2 and 3. These devices are in the form of a chip, with an electrode array aligned along at least two axes. The individual electrodes are coated with a solid phase material. In some cases, all of the electrodes are coated with the same material; in other cases, the coatings differ from electrode to electrode or form a coating gradient along a capillary connecting two or more electrodes. The chips can optionally be interfaced with an analytical device such as a mass spectrometer or a capillary electrophoresis device.

Although the design of the chips can vary widely, the operation of the chips is similar irrespective of the design. In one of the simplest designs (FIG. 2), electrodes 20, 30, 50, 70, and 80 are electrically connected to contact points 22, 32, 52, 72, and 82, respectively. A sample containing, for example, chromosomal DNA to be isolated is introduced at electrode 20 at ambient pressure. In addition to the nucleic acids to be isolated, the sample can include salt (e.g., 50 to 350 mM sodium chloride) and various impurities. Electrode 20 is coated with a material that absorbs the sample (e.g., an ion-exchange resin such as DEAE).

The chip 25 is placed within the sample chamber of a pressure-modulation apparatus (e.g., the apparatus described at pages 4–9 and 29–44 and in FIGS. 1 and 4 of PCT Appln. No. US/96/03232, which was given Ser. No. 08/793,213 in the U.S. National Phase and issued on Mar. 14, 2000 as U.S. Pat. No. 6,036,923 adapted to supply a switchable electrical voltage at the contact points 22, 32, 52, 72, and 82. A voltage potential is supplied between electrodes 20 and 30 (i.e., electrode 20 is the anode and electrode 30 is the cathode) while the system is at ambient pressure. The potential causes the sample to flow through capillary 40, which is filled with a size-exclusion filtration material (e.g., 0.5%–2% agarose) that retains large cellular debris but allows nucleic acids, proteins, lipids, and other small cellular components to pass through.

The flow-through then passes through to electrode 50, which is coated with an anion-exchange resin. Nucleic acids in the molecule are trapped at electrode 50, while other components in the flow-through continue through the aqueous solution in capillary 60, and ultimately, to electrode 30. Electrode 30 includes a material (e.g., polyacrylamide) that traps the impurities that reach it. The voltage potential between electrodes 20 and 30 is then discontinued.

The pressure in the system is increased to a moderately elevated level (e.g., 500 to 10,000 psi). A voltage potential is set up between electrodes 50 (anode) and 80 (cathode). The moderate pressure causes the smallest nucleic acids (e.g., less than 5,000 bp) to dissociate from the anion-exchange resin at electrode 50, and the potential causes the nucleic acid to migrate through the liquid phase in capillary 90 and finally into electrode 80, which includes a reservoir. The potential is discontinued.

The pressure in the system is increased to a more elevated level (e.g., 12,000 to 100,000 psi). A voltage potential is set up between electrodes 50 (anode) and 70 (cathode). The high pressure causes the remaining nucleic acids to dissociate from the anion-exchange resin at electrode 50, and the potential causes the nucleic acid to migrate through the liquid phase in capillary 75 and finally into electrode 70, which includes a reservoir. The potential is discontinued, the pressure is lowered to ambient pressure, the chip is removed from the pressure-modulation apparatus, and the large nucleic acid fraction, including the chromosomal DNA, can be removed from electrode 70.

In another design (FIG. 3), electrodes 100, 110, 120, 130, 140, 170, 200, and 220 are electrically connected to contact points 102, 112, 122, 132, 142, 172, 202, and 222, respectively. A whole blood sample is introduced at electrode 100 at ambient pressure. Electrode 100 is coated with a wicking material that absorbs the sample.

The chip 190 is placed within the sample chamber of a pressure-modulation apparatus adapted to supply a switchable electrical voltage at the contact points 102, 112, 122, 132, 142, 172, 202, and 222. A voltage potential is supplied between electrodes 100 (anode) and 120 (cathode) while the system is at ambient pressure. The potential causes the sample to flow through liquid-filled capillaries 105 and 125 and electrode 110. At the junction between electrode 110 and capillary 125, a filter 114 prevents white blood cells from passing. An example of a suitable filter is the HEMAFILO Nucleopore membrane (Corning Separations Division, Acton, Mass.), a polymeric microporous track-etch polycarbonate having a pore size of 4.7–5.0 μm. Thus, the white blood cells become trapped at electrode 110, while red blood cells continue to migrate to electrode 120.

The pressure is increased momentarily (e.g., to 80,000 psi, 120,000 psi, or higher), lysing the cells at electrodes 110 and 120, and irreversibly inactivating any nucleases present in the cell lysates. The pressure is then restored to ambient pressure. A potential (e.g., 100–200 V, or a constant current, e.g., 20–40 mA, or a constant power, e.g., 500 watts) is then provided between electrodes 110 (anode) and 220 (cathode). Capillary 115 contains a sizeexclusion material or an ion-exchange material, for example, that can retain large cellular debris but allow nucleic acids, proteins, lipids, and other small cellular components to pass through.

The flow-through then passes through to electrode 140, which is coated with oligo-dT, and through to electrode 170, which is coated with an anion-exchange resin. RNA in the white blood cell lysate is trapped at electrode 140 and DNA in the white blood cell lysate is trapped at electrode 170, while the remaining components in the flow-through continue through the aqueous solution in capillary 176 and ultimately to electrode 220. Electrode 220 includes a reservoir that traps the impurities that reach it. The potential is then discontinued.

A potential is supplied between electrodes 140 (anode) and 130 (cathode). The potential causes the RNA to dissociate from the solid phase at electrode 140, migrate through the liquid phase in capillary 144, and finally to electrode 130, where a reservoir traps the RNA. The potential is discontinued.

The pressure in the system is then increased to an elevated level (e.g., 20,000 to 100,000 psi), and a potential is supplied between electrodes 170 (anode) and 200 (cathode). The pressure causes the DNA to dissociate from the solid phase at electrode 170, and the potential causes the nucleic acid to migrate through the liquid phase in capillary 174, and finally to electrode 200, where a reservoir traps the DNA. The potential is discontinued, the chip is removed from the pressure-modulation apparatus, the purified white blood cell RNA can be removed from electrode 130, and the purified white blood cell DNA can be removed from electrode 200.

There may be multiple versions of this device or consumables for use with the device that are optimized for various applications and sample sizes. For instance, a miniature version can be highly parallel and/or interface into a downstream biochip. Examples of sample sizes include 1 fl, 1 pl, 1 nl, 1 μl, 1 ml, 10 ml, and intermediate sizes.

The chips can be made from any suitable material which can be planar in form and worked by conventional processes. Base materials include plastics, such as polypropylene or polytetrafluoroethylene (PTFE); inorganic oxides, such as silica, glass and ceramics; metals; and semiconducting materials, such as silicon. The contact points and electrodes are made of conductive materials, including metals (such as gold, silver, copper, aluminum or iron), semiconductors, conductive polymers, and aqueous solutions, optionally stabilized by fabrics, gels, and the like.

The chips can be designed such that the fluids in the capillaries are in direct fluid contact with the reaction chamber of the pressure-modulation apparatus. More preferably, the chips can be designed as a closed system with a diaphragm (FIG. 4), a piston (FIG. 5), or a hydrophobic valve (FIG. 6), which relays the pressure from the reaction chamber to the capillaries and electrodes.

Figure 4A:
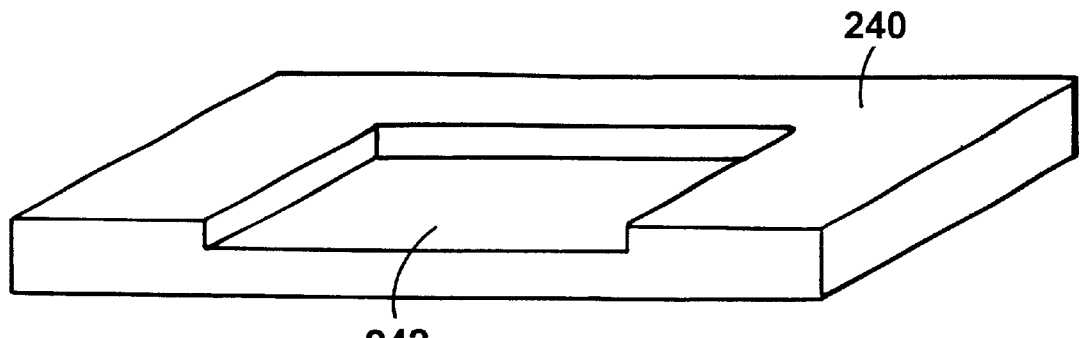
FIG. 4A is a cut-away perspective view of a chip of the invention.
Figure 4B:
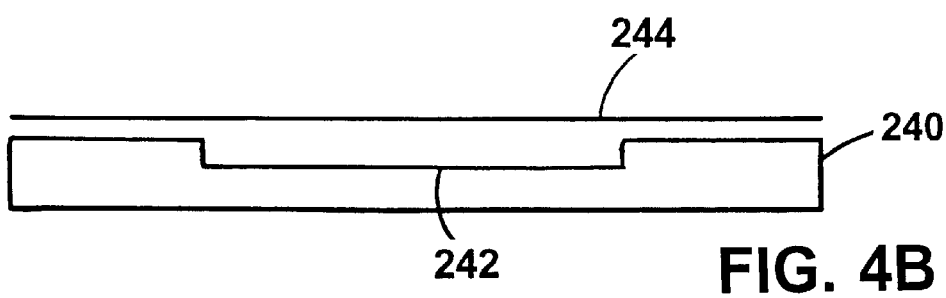
FIG. 4B is an exploded side view of a chip of the invention that includes a diaphragm for relaying pressure.
Figure 4C:
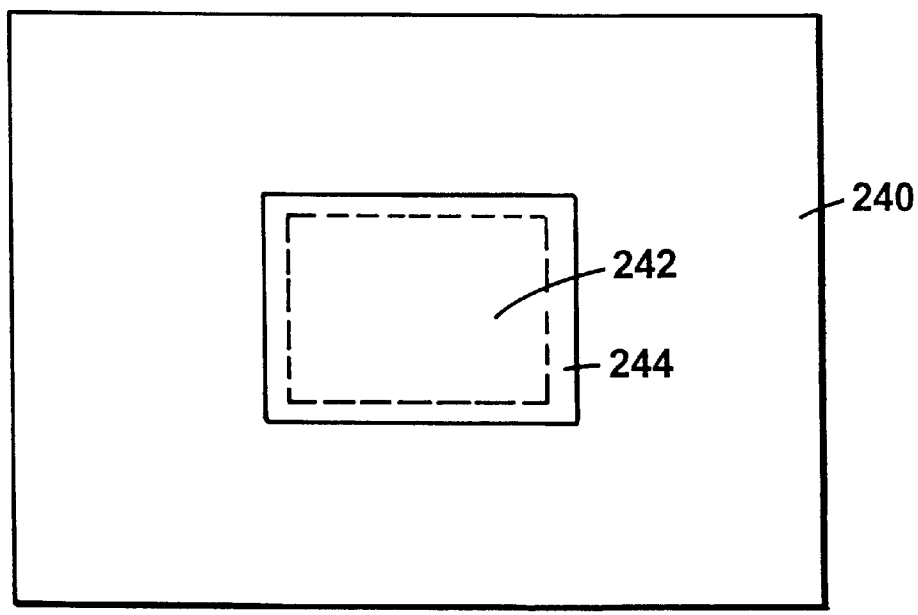
FIG. 4C is a top view of a chip of the invention that includes a diaphragm for relaying pressure.

As shown in FIGS. 4A to 4C, the chip 240 can include a recessed area 242, in which the electrode array is situated. A flexible, elastic membrane 244 spans the recessed area 242, to form a diaphragm. One or both surfaces of the membrane can be flexible. The membrane transmits external pressure to the electrode array, while simultaneously providing a hermetic seal that prevents fluids from being transferred.

Figure 5A:
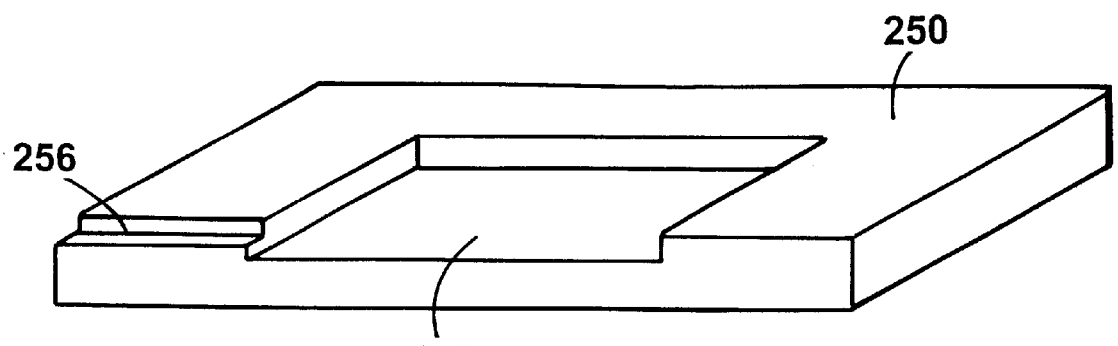
FIG. 5A is a cut-away perspective view of a chip of the invention.
Figure 5B:
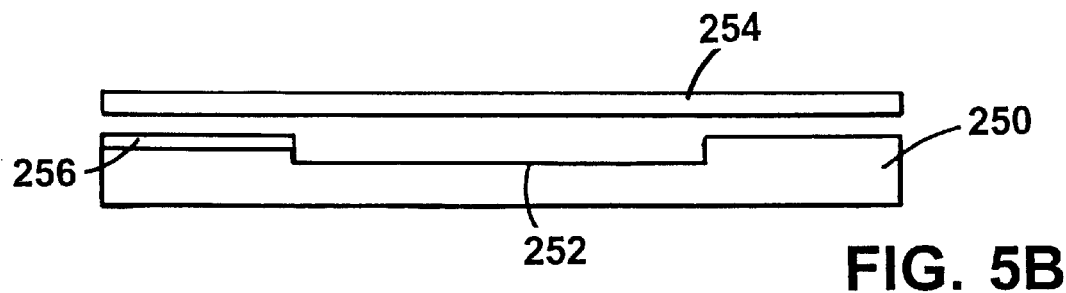
FIG. 5B is an exploded side view of a chip of the invention that includes a hydrophobic valve for relaying pressure.
Figure 5C:
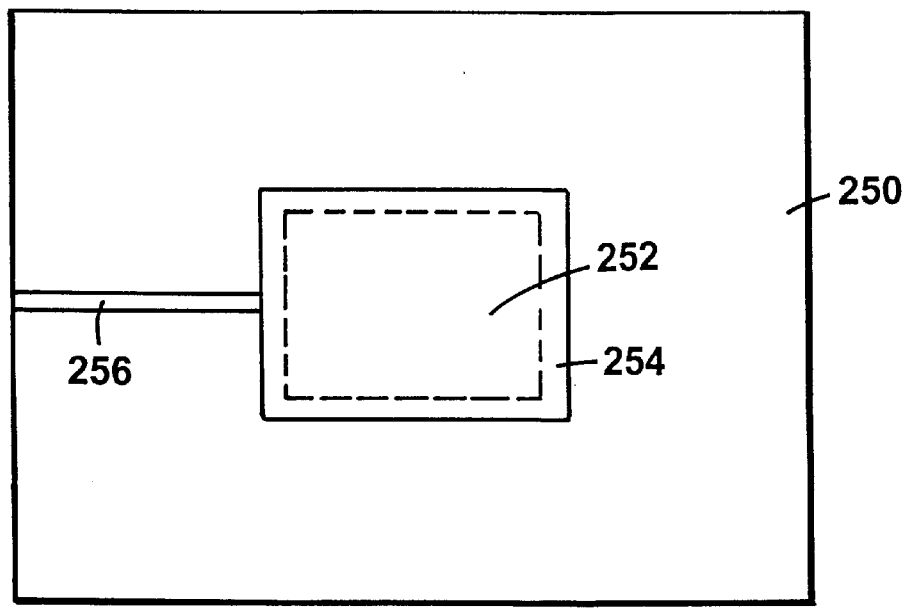
FIG. 5C is a top view of a chip of the invention that includes a hydrophobic valve for relaying pressure.

The chip 250 shown in FIGS. 5A to 5C also includes a recessed area 252, in which the electrode array is situated. A solid lid 254 is placed over the recessed area. A channel 256 is drilled through one side of the chip, leading into the recessed area 252. The wall of the channel 256 is precoated with a hydrophobic material, such that water and other fluids are unable to traverse the length of the channel 256 under ambient conditions. As the pressure is increased, however, the fluids overcome the hydrophobic interactions and pass through the channel 256, thereby modulating the pressure within the recessed area 252.

Figure 6A:
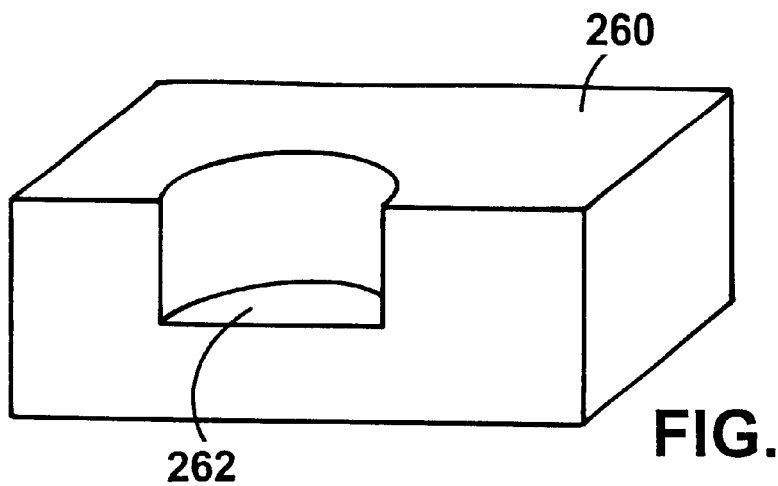
FIG. 6A is a cut-away perspective view of a chip of the invention.
Figure 6B:
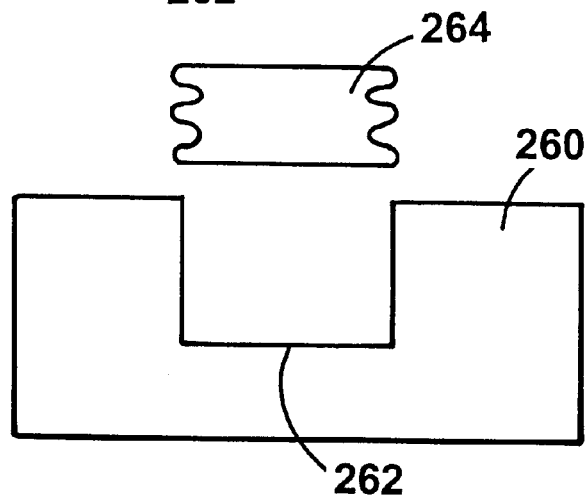
FIG. 6B is an exploded side view of a chip of the invention that includes a compressible piston for relaying pressure.
Figure 6C:
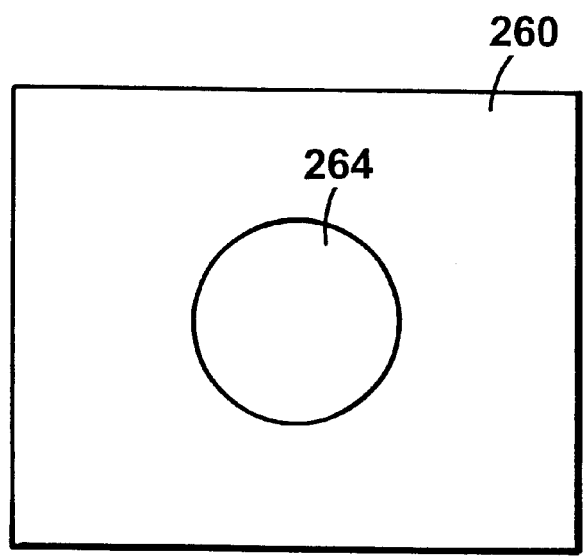
FIG. 6C is a top view of a chip of the invention that includes a compressible piston for relaying pressure.

In a third design, shown in FIGS. 6A to 6C, a chip 260 includes a recessed area 262, in which the electrode array is situated. A compressible, elastomeric piston 264 is mounted in the recessed area 262. When the pressure in the reaction chamber is increased, the piston 264 becomes compressed, thereby increasing the pressure at the electrode array without allowing fluid transfer between the reaction chamber and the electrode array.

In addition, it is possible to retain fluid in narrow capillaries, such as capillaries having diameters in the range of 10 to 1000 microns, without needing an external restraint, provided that the surface of the capillary has a polarity (surface energy) which permits the fluid to wet the capillary surface. Processes may be performed in such capillarity-filled capillaries without an external cover, if the space above the open capillary is saturated with the vapor phase of the fluid. Alternatively, any sufficiently non-wettable (hydrophobic or solvophobic) surface can be used to close the upper surface of the capillaries, and thereby allow stacking of chips without having the fluid in the capillary spread beyond the capillary by wetting the film. For aqueous solutions, a sheet of polypropylene or PTFE, or a coating on the back of the next chip in the stack, could serve the purpose.

Disposable Two-Syringe Device

In an example of still another embodiment of the invention, the sample is placed into a first (loading) syringe having a DEAE resin cartridge attached at the narrow end. This system must have a very small resin chamber so that high pressures can be generated and the materials must be able to withstand the high pressures. The plunger is slowly depressed, so as not to create a significant pressure gradient. As the sample is loaded onto the resin, the waste is discarded. Low salt (e.g., 10 to 300 mM) buffer is placed in the syringe. The buffer can contain magnesium and other cofactors necessary for downstream enzymatic techniques. A measured quantity (e.g., 100 μl to 10 ml) of the buffer is used to wash the resin to remove non-DNA contaminants.

A second (collection) syringe is added to the first. The resistance of the plunger of the second syringe is adjusted such that the pressure needed to move the loading syringe causes the dissociation of the nucleic acid from the resin. The resisting force exerted by the collection syringe can be adjusted by means of low-angle threads in the syringe and piston. The angle of the threads can be adjusted to change the pressure. For applications where consistency of yield and purity are crucial, the pressurizing step can be carried out by, or with the aid of, a machine that maintains a consistent pressure and flow rate, such as an expression chamber with a check valve.

Another version of this system would use a device which applied an equal force to two opposing pistons and (with much less force) moved the two syringes simultaneously to achieve a flow. In another version, two pistons supply force, with a small pressure differential between them. This system can be immersed in a pressurizing medium (such as water) so as to avoid the use of pressure resistant materials and small resin capacity in the disposable component.

Sample Cell for Pressurization

Figure 9:
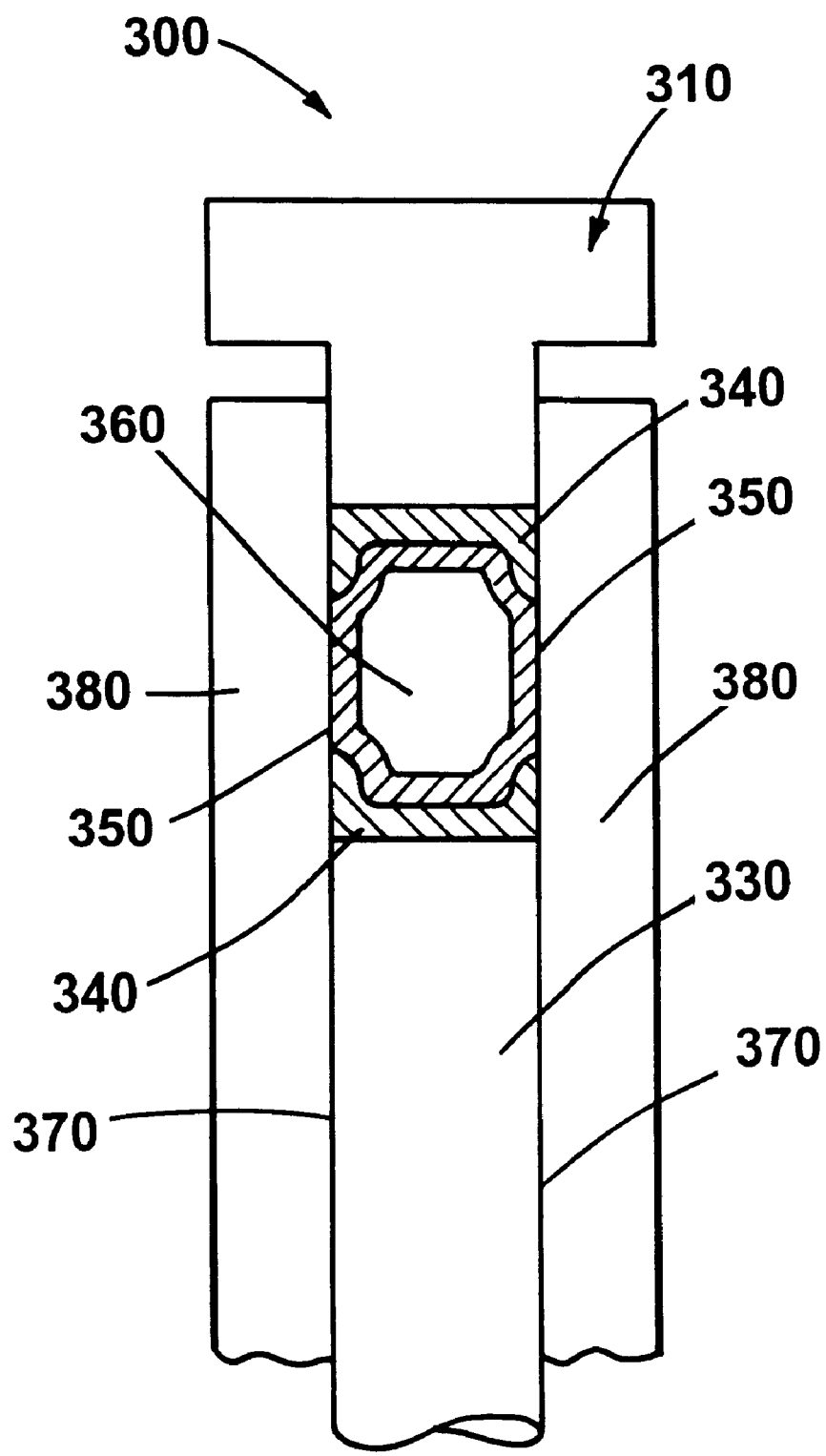
FIG. 9 is a view of a sample cell for pressurization.

FIG. 9 is a view of a cylindrical chamber for pressurization in a pressure modulation apparatus. The chamber 300 includes a rigid closure 310, a sample cell 320, and a piston 330. The piston communicates the pressure outside the chamber 300 to the sample cell 320. The sample cell 320 also includes rigid end caps 340, flexible walls 350, and a sample compartment 360. The rigid end caps 340 prevent extrusion of the flexible walls 350 into the clearance gap 370 between the piston 330 and cylinder walls 380. The flexible walls 350 allow deformation of the sample cell 320 to allow compression of the sample in the sample compartment 360.

The following illustrative examples are not intended to limit the scope of the invention.

EXAMPLE 1

DNA Isolation and Purification in an Anion-Exchange Cartridge:

DNA samples were separated using a Qiagen DEAE anion-exchange resin (Qiagen, Inc., Santa Clarita, Calif.) at ambient and elevated pressures. The DEAE resin was packed into a 9 mm×4 mm I.D. (5 mm O.D.) stainless steel 'half-length column' capped with titanium frits with a 2 μm pore size (Valco Instrument Company, Inc., Houston, Tex.). Two half-length columns, one containing resin and the other acting as a spacer and devoid of resins were placed into a column holder. The column holder was a metal tube with an inner diameter of 5 mm and syringe fittings at the ends to allow fluid to flow through the columns.

Pressure elution of DNA was performed using a pressure apparatus as described at pages 29 et seq. of PCT Appln. No. US/96/03232, which was given Ser. No. 08/793,213 in the U.S. National Phase and issued on Mar. 14, 2000 as U.S. Pat. No. 6,036,923, controlled by a microcomputer with LAB-VIEW™ software (National Instruments, Austin, Tex.). The columns were inserted into a pressure chamber adapted to receive the columns. Liquid was injected and removed from the chamber using a series of pneumatic valves and pistons as described in the '232 application, allowing for elution of DNA from the column while maintaining elevated pressure within the column.

The DEAE column was initially washed with 1 ml high salt elution buffer (1.25 M sodium chloride; 50 mM Tris-HCl, pH 8.5; 15% ethanol) and equilibrated with 1 ml equilibration buffer (750 mM sodium chloride; 50 mM MOPS, pH 7.0; 15% ethanol; 0.15% Triton X-100). Approximately 300 μl of 21 μg/ml DNA in loading buffer (1 M potassium acetate; 33 mM NaCl; 33 mM Tris-HCl, pH 5; 8 mM EDTA), was injected into the packed column over five minutes, in four 1 minute intervals. 1 ml of MO washing buffer (containing 1 M NaCl; 50 mM MOPS, pH 7.0; 15% ethanol) was then injected through the holder to remove any remaining contaminants, followed by 200 μl of elution buffer to displace the MO washing buffer prior to elution either at atmospheric or elevated pressures. Elution buffers used during the DNA elution step contained 50 mM Tris-HCl, pH 8.5, and various concentrations of sodium chloride Four consecutive 300 μl elution fractions were collected during each experiment. Each fraction was collected over a three minute interval, in which a 100 μl pressure wash step with the elution buffer was performed each minute. Experiments at atmospheric pressure were performed with identical elution steps, using a syringe to deliver the elution salt solutions through the column holder.

DNA in the collected samples was quantified using OliGreen DNA binding dye (Molecular Probes, Eugene, OR). To reduce the background signal and increase sensitivity, the salt concentration in the DNA assay solutions to be assayed was first diluted 20–200 fold with TE buffer (10 mM Tris-HCl, 1 mM EDTA, pH 7.5) and then complexed with the OliGreen dye (20,000:1 DNA:dye in volume). Fluorescence emission intensity ($\lambda_{em}$=520 nm, $\lambda^{ex}$=480 nm) of the DNA/OliGreen solution was measured with an ISS PCI spectrofluorometer (ISS, Inc., Champaign, Ill.), without background subtractions. Quantitation of DNA was made by comparing the measured intensity with calibration curves obtained from known DNA concentrations. Recovery of DNA in the elution fractions was calculated by dividing total DNA in the elution fractions with the total DNA bound in the column, (i.e., total DNA loaded minus DNA in flow-through and MO washing solutions).

At elevated pressures, $\lambda$DNA (Worthington Biochemical Company; Freehold, N.J.) was released from the DEAE resin with a buffer of lower salt concentration, as shown in Table 1. The percentages given in the table are percent recoveries, and numbers in parentheses after the percentages are the number of times the corresponding experiments were carried out. The error range was calculated to be approximately 5% based on the duplicated data.

TABLE 1

$\lambda$DNA Purification with Low Salt Buffer at Various Hyperbaric Pressures

| [NaCl] (M) in Tris Buffer | Pressure (MPa) | | | |
|---|---|---|---|---|
| | 0.1 | 90 | 170 | 220 |
| 0.10 | trace (1) | | trace (1) | 40% (1) |
| 0.25 | trace (2) | | 20% (3) | 100% (1) |
| 0.40 | | | 25% (1) | |
| 0.50 | trace (2) | 15% (1) | 70% (2) | 60% (1) |
| 0.75 | trace (2) | 15% (1) | 100% (2) | trace (1) |
| 1.00 | 100% (1) | | 100% (1) | |

Table 1 shows a correlation: the higher the pressure, the lower the salt concentration needed for dissociation. At 0.1 MPa (i.e., atmospheric pressure), 1 M sodium chloride was required for more than just a trace amount (i.e., less than 10%) of DNA to be eluted. At 90 MPa (about 12,500 psi), the DNA showed a slightly increased tendency to dissociate; at 170 MPa (about 24,000 psi), 70% of the $\lambda$DNA was dissociated with 0.50 M NaCl. 100% of the $\lambda$DNA dissociated with 0.25 M NaCl at 220 MPa (about 32,000 psi). Interestingly, less of the DNA eluted at this pressure when the salt concentration was raised, possibly due to a phase change in the silica resin that is aided by electrostatic shielding in the high salt environment. A similar effect is seen at lower salt concentrations and higher pressures.

A follow-up experiment included three different sizes of DNA. Human cell extract high molecular weight DNA K562 (number of bp is unknown; Pharmacia Biotech, Inc., Piscataway, N.J.) and $\lambda$DNA (~48.4 kb) behaved similarly. Both yielded a 25% recovery with 0.40 M NaCl Tris-HCl buffer at 170 MPa. On the other hand, 100% recovery of the plasmid pKK223-3 (about 4.6 kb DNA) was observed under the same conditions.

Figure 7:
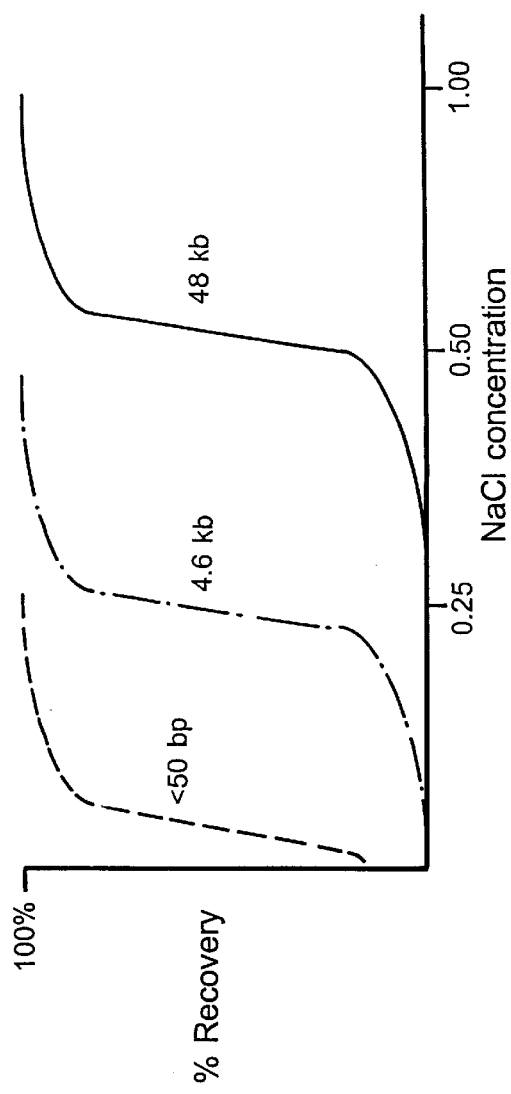
FIG. 7 is a graph of percent recovery of nucleic acids as a function of sodium chloride concentration at constant pressure for three sizes of DNA: 50 bp ( . . . ) 4.6 kb (- - -), and 48.4 kb (—).

To test the effect of salt concentration for three different sized nucleic acids (i.e., 50 bp, 4.6 kb, and 48.4 kb), the pressure was held at 23,600 as the concentration of sodium chloride was increased from 0 to 1 M. The nucleic acids were detected as they eluted from the cartridge. The results are shown in the graph in FIG. 7. Most of the smallest nucleic acid, 50 bp, was eluted by 100 mM sodium chloride (i.e., as indicated by the dotted line). The 4.6 kb fragment was eluted at 250 mM, as shown by the dashed line. The solid line indicates that 500 mM sodium chloride was required to elute the largest nucleic acid, 48.4 kb. Thus, the nucleic acids can be separated on the basis of size by varying the salt concentration.

Figure 8:
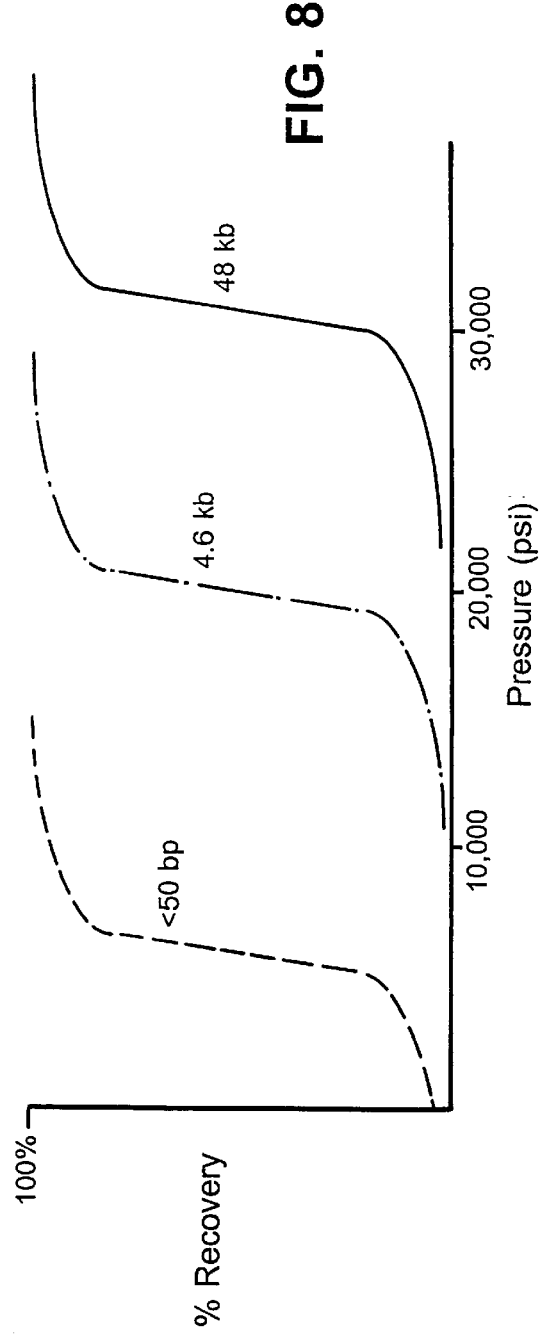
FIG. 8 is a graph of percent recovery of nucleic acids as a function of pressure at constant sodium chloride concentration for three sizes of DNA: 50 bp ( . . . ), 4.6 kb (- - -), and 48.4 kb (—).

The effect of pressure was also studied, using the same three nucleic acid fragments. In this experiment, the sodium chloride concentration was held constant at 250 mM, as the pressure was increased from 14 to 40,000 psi. The nucleic acids were detected as they eluted from the cartridge. The results are shown in the graph in FIG. 8. Most of the smallest nucleic acid, 50 bp, was eluted at around 7,000 psi, as indicated by the dotted line. The 4.6 kb fragment was eluted at about 20,000 psi, as shown by the dashed line. The solid line indicates that approximately 32,000 psi was necessary to elute the largest nucleic acid, 48.4 kb. Thus, the nucleic acids can be separated on the basis of size by varying the elution pressure.

To test the specificity of the resin for nucleic acids, bovine serum albumin (BSA) was applied to the DEAE column. Serum albumins are multivalent and highly absorptive, and are the most abundant proteins in mammalian blood. It is therefore highly desirable that any DNA purification procedure for isolating DNA from blood be capable of separating BSA from DNA. Indeed, all of the protein was recovered in the flow through and MO washing solutions.

Agarose gels were used to check the integrity of DNA in the eluent solutions. Where sufficient DNA was recovered for analysis, the DNA molecules were found to be intact. In the remaining cases, there was not enough DNA to test on a gel. The DNA in the elution solutions was also quantified, using PicoGreen, a dye specific for double-stranded DNA, PicoGreen (Molecular Probes, Eugene, Oreg.). The dye indicated that the majority of DNA (i.e., about 90% of the DNA) was still double-stranded after applying pressure with a high concentration of salt.

EXAMPLE 2

Restriction Digestion of Eluate without Desalting:

pCMV-SV40T plasmid was isolated from 1.5 ml of an overnight culture of an JM109 *E. coli* strain by alkaline lysis (Sambrook et al., Molecular Cloning: A Laboratory Manual, 2nd ed., Cold Spring Harbor Laboratory Press: Plainview, N.Y., 1989, pp. 1.25–1.26). 1.5 ml of an overnight bacterial culture was placed in a microcentrifuge tube and spun for 30 seconds at 12,000 g. The medium was removed and the cells were resuspended with vigorous vortexing in 100 $\mu$l of a solution containing 50 mM glucose, 25 mM Tris-HCl (pH 8.0), and 10 mM EDTA (pH 8.0). 200 $\mu$l of a freshly made solution of 0.2 N NaOH (containing 1% sodium dodecyl sulfate, SDS) was added, and the tube was inverted five times. 150 $\mu$l of ice cold solution III (prepared by mixing 60 ml of 5 M potassium acetate, 11.5 ml of glacial acetic acid, and 28.5 ml of water) was added, then the sample was gently vortexed and incubated on ice for 4 minutes. The sample was centrifuged at 12,000 g for 5 minutes. The cleared, neutralized supernatant was transferred to a fresh tube and water was added to a final volume of 700 $\mu$l. 300 $\mu$l of the sample was purified using the Qiagen™ #12129 plasmid kit (Santa Clarita, Calif.) without the final isopropanol precipitation. Another 300 $\mu$l of the sample was loaded onto a cartridge and processed as described in Example 1. The plasmid was eluted with 400 mM NaCl at 23,6000 psi. 45 $\mu$l of purified plasmid solution was mixed with 55 µl of buffer (containing 18 mM Tris-HCl pH 8.0, 18 mM MgCl$_2$, 1.8 mM dithiothreitol, and 180 µg/ml of BSA). A restriction digest reaction was initiated by adding 0.5 µl (40 units) of BamHI enzyme (Promega, Madison, Wis.) and incubated for 1 hour at 37° C.

The results were analyzed by agarose gel electrophoresis. The gel was stained using SYBR1 (Molecular Probes; Eugene, Oreg.). No digestion was seen with the Qiagen™ purified DNA, whereas the pressure eluted DNA showed two bands, indicating digestion of the plasmid at the two BamHI sites. This result demonstrated that, in contrast to a traditional nucleic acid elution procedure, DNA eluted under high pressure can be cleaved by a restriction enzyme without a precipitation or desalting step, other than a 1:1 dilution into reaction buffer.

EXAMPLE 3

Protein Expression in Mammalian Cells Utilizing Plasmid DNA Isolated and Purified by Hyperbaric Pressure The vector pCMV-SV40TAg, which encodes the large tumor antigen (TAg) of the SV40 virus, was transformed into a bacterial strain, JM109, and isolated by standard alkaline lysis procedure (Sambrook et al. *Molecular Cloning: A Laboratory Manual*, Cold Spring Harbor Laboratory Press; Plainview, N.Y., 1989) essentially as described in Example 2. 1.0 ml of the sample was purified using the Qiagen #12129 plasmid kit (Santa Clarita, Calif.). Another 1.0 ml of the sample was aliquoted into three equal portions and processed batchwise as described in Example 1. The plasmid was eluted with 500 mM NaCl at 29,000 psi. The solution containing the purified pCMV-SV40TAg plasmid was ethanol precipitated and resuspended in sterile water.

A transient protein expression assay was performed to compare the purity and quality of the plasmid prepared using hyperbaric pressure with that of the plasmid prepared with the Qiagen kit. To assay the level of TAg protein expression, a monkey kidney cell line, BSC 40, was transiently transfected with either the pressure purified or the Qiagen purified pCMV-SV40TAg plasmid using a standard calcium phosphate transfection procedure (Ausubel et al., *Current Protocols in Molecular Biology*, John Wiley & Sons; New York , 1987 pp. 9.1.1 to 9.1.4). Western blot analysis was performed according to standard procedures (ibid., pp. 10.2.1 and 10.8.1). The results of this experiment indicated that pCMV-SV40TAg DNA prepared using hyperbaric pressure was three- to five-fold more efficient at directing TAg protein expression compared with the same plasmid prepared using the Qiagen kit. These results demonstrate the quality and stability of plasmid DNA following isolation by hyperbaric pressure.

EXAMPLE 4

Isolation of total RNA on a DEAE Anion-Exchange Cartridge:

BSC40 cells that stably express TAg were lysed by the method of Chomczynski et al. (*Anal. Biochem.*, 162:156–159, 1987). 1 ml RNA STAT-60™ (Tel-test, Inc., Friendswood, Tex.) was added directly to the cells. After incubating at room temperature for 5 minutes, the cells were scraped from the plate, homogenized by pipetting, and transferred to a sterile microcentrifuge tube. After addition of 0.2 ml chloroform, the solution was mixed vigorously for 15 seconds and the upper aqueous phase was separated by centrifugation. Following precipitation of the RNA with isopropanol, the RNA was pelleted by centrifugation in a microcentrifuge, and resuspended in 50 µl of sterile RNAse-free water. 10 µl of the RNA sample was then mixed with 500 µl of equilibration buffer (containing 750 mM sodium chloride; 50 mM MOPS, pH 7.0; 15% ethanol; and 0.15% Triton X-100).

Qiagen DEAE anion-exchange resin was packed in the "half-column" as described in Example 1, and washed with 1 ml equilibration buffer. 300 µl RNA sample was injected onto the DEAE column over 3 minutes. Then, 1 ml MO buffer (containing 1 M NaCl; 50 mM MOPS, pH 7.0; 15% ethanol) and 200 µl elution buffer (containing 250 mM sodium chloride and 50 mM Tris, pH 8.5) was applied to wash the column. Four consecutive 100 µl and three 300 µl elution fractions were collected at 23,600 psi. After taking the DEAE column out of the pressure flow apparatus, the column was washed with 1 ml of high salt buffer (containing 1.25 M sodium chloride; 50 mM Tris-HCl, pH 8.5; and 15% ethanol).

RNA in the collected samples was quantified using Oli-Green DNA binding dye. To reduce background signals, RNA assay solutions were diluted 125-fold with TE buffer (containing 10 mM Tris-HCl and 1 mM EDTA, pH 7.5), which contained 1200-fold diluted OliGreen. Fluorescence emission intensity ($\lambda_{ex}$=485 nm, $\lambda_{em}$=580 nm) was measured with a FLUOROCOUNT™ microplate fluorometer (Packard Instrument Company, Meriden, Conn.), without background subtractions. The quantity of RNA was estimated by comparing the measured intensity with calibration curves obtained from known λDNA concentrations. The recovery of RNA in the elution fractions was calculated by dividing total RNA in the elution fractions by the total RNA bound in the column.

It was found that at 23,600 psi, more than 60% of RNA was released from the DEAE resin in the first 4 fractions. The other three fractions contained about 40%; thus 100% recovery was achieved. The high salt wash solution was analyzed to verify this result; indeed, no RNA was detected in the subsequent high salt wash solutions. To compare the integrity and purity of RNA isolated using hyperbaric pressure with that of the original RNA sample preparation, both samples were analyzed on a 0.8% agarose gel. The results indicated that there was no significant degradation of the 28S and 18S rRNA following isolation on the DEAE anion-exchange cartridge with hyperbaric pressure. These results suggested that total RNA was effectively isolated using the high pressure procedure without shearing or degradation by RNases. The estimated yield of RNA, based on the gel electrophoresis, was consistent with the estimation made by fluorescence assay. Thus, it is shown that high pressure elutes RNA from the column at lower salt concentration while preserving physical integrity.

EXAMPLE 5

Purification of Messenger RNA (mRNA) from a Eukaryotic Sample:

Two cartridges containing a solid phase are arranged in serial order, such that eluent from the first cartridge enters the second cartridge. The first cartridge is packed with an activated acidic DEAE activated anion exchange resin and the second is packed with a resin containing covalently linked polythymidine (poly-dT) resin.

An mRNA standard (positive control) is purified by standard methods using the POLY(A)PURE™ Kit (Ambion, Austin, Tex.). A salt concentration is found (i.e., by multiple trials) at which poly-da mRNA is poorly bound to poly-dT resin at atmospheric pressure, but is more tightly bound at high pressure. Samples are loaded onto the cartridge containing the poly-dT resin, in a buffer containing 100 mM NaCl and 10 mM Tris-HCl, pH 7.2, at atmospheric pressure.

The samples are then eluted with 300 µl of buffer containing 10 mM Tris-HCl (pH 8.0) and NaCl concentrations of 0 to 100 mM in increments of 10 mM. The salt is removed from the sample by washing twice in 10 mM Tris-HCl (pH 8.0) using a Macrocon-100™ spin-filter (Millipore). The experiment is repeated at 29,000 psi for each sample that has a different salt concentration. A buffer which gives poor binding at atmospheric pressure, but improved binding at high pressure is selected and referred to as "solution A".

NIH 3T3 cells, grown in culture, are lysed by standard procedures (Chomczynski et al., supra) and total RNA is isolated on the DEAE column as described in Example 4. The cell debris is removed by centrifugation. The sample is applied to the double anion-exchange/poly-dT column. The column is washed with 300 µl of solution A. The column is then washed at 25,000 psi with 300 µl of solution A, thereby directly transferring the mRNA from the anion-exchange resin to the poly-dT resin. The pressure is then lowered to atmospheric pressure and the resin is washed with 300 µl of either solution A or distilled water to recover the mRNA. The sample is analyzed for purity by reverse transcriptase= polymerase chain reaction (RT-PCR) for specific target transcripts, agarose gel electrophoresis, UV spectroscopy, and a protein binding dye assay. To determine the quality and integrity of the mRNA isolated utilizing this procedure, β-actin mRNA, for example, can be amplified using β-actin primers in RT-PCR (Promega, Madison, Wis.). The resulting DNA products can then be analyzed on a 1.0% agarose gel and compared with cDNA product resulting from the RT-PCR procedure using the positive mRNA control. These results indicate that mRNA is effectively isolated on a poly-dT cartridge, transferred to a poly-da cartridge using 25,000 psi, and effectively recovered for subsequent analysis.

EXAMPLE 6
Detection of p53 Mutations in Human Malignancies Using Hyperbaric Pressure Purified RNA:

Total RNA obtained from tumor samples is prepared by a combination of the method of Chomczynski et al. (supra) and the hyberbaric DEAE column purification as described in Example 4. The homogenized human sample is lysed with 8 M urea and 50 mM Tris-Cl buffer (pH 8.0). 500 µl urea solution is then loaded onto the activated DEAE resin, which is packed in a cartridge at atmospheric pressure. Total RNA will elute off the column at 29000 psi. The mRNA of interest (i.e., p53) is amplified by reverse transcriptase-polymerase chain reaction (RT-PCR) using p53-specific primers (Promega, Madison, Wis.). The resulting DNA product is then sequenced with the dideoxy chain termination method using a Sequenase 2.0 kit (United States Biochemicals), then analyzed for mutations by comparing to the p53 consensus sequences. This therefore indicates that hyperbaric pressure RNA isolation is an effective and simplified procedure to obtain RNA molecules from cells.

EXAMPLE 7
Isolation of RNA from Human Whole Blood:

300 ml of the whole blood with anticoagulant, e.g., heparin, is loaded onto a DEAE anion-exchange cartridge over three minutes as described in Example 1. The column is then pressurized to 60,000 psi to cause cell lysis and nucleic acid molecules bind with the DEAE resin. Subsequently, RNA is eluted at 29,000 psi as described in Example 4, collected in consecutive fractions, precipitated with isopropanol, and resuspended in 30 ml of RNase-free water.

As a control, total RNA is extracted by the method of Chomczynski (*Biotechniques,* 15:532–536, 1993). 300 µl of whole blood is mixed with 1.0 ml of red blood cell lysis solution (RBCS; containing 40 mM ammonium chloride, 10 mM potassium hydroxide, 7.5 mM potassium acetate, 2.5 mM sodium bicarbonate, 0.125 mM EDTA, and 0.1% glacial acetic acid). After 10 minutes at 4° C., the residual red blood cells are pelleted by centrifugation (30 seconds at 12,000 g). An additional 1.0 ml RBCS is added to the pellet and mixed thoroughly. The centrifugation step described above is repeated. The supernatant is removed and the leukocyte pellet is resuspended in 350 µl of leukocyte lysis solution (LLS: 4 M guanidinium isothiocyanate. 0.1 M β-mercaptoethanol, 10 mM sodium citrate, pH 7.0, 0.5 M lauryl sarcosine, and 2.0% Triton X-100). The tube is vortexed vigorously prior to addition of 350 µl 64% ethanol.

The quality and integrity of total RNA eluted from the column is analyzed on a native 1.0% agarose gel stained with ethidium bromide. Results show clear bands of the 28S and 18S rRNA. Further, the RNA sample is examined for the existence of β-actin mRNA using RT-PCR as described in Example 5. The results show a distinctive signal originating form β-actin in the purified blood sample.

EXAMPLE 8
Pressure Effects on Ion-Exchange Electrophoresis

5 µl 384 µM rhodamine-labeled 21-mer deoxyoligonucleotide was mixed with 100 µl of Qiagen silica ion-exchange resin in 25 mM TBE buffer. The resin was placed in a cartridge composed of acrylic that had four reservoirs for holding resin or liquid. An electrode was molded into the bottom for each reservoir and contacted the cartridge cap by means of a wire glued to the outside of the cartridge. The cartridge was filled with borate buffer and a cap with an o-ring was placed on top to form a seal and act as a piston. The cartridge was designed such that it could be plugged into four electrical leads in the cap of a pressurizing apparatus. The pressurizing medium was silicone oil.

As a control, 1.2 mA of electric current was applied at 5,000 psi of pressure for 15 minutes. No effect was observed. However, when the same current was applied at 25,000 psi of pressure for 15 minutes, the labeled oligonucleotide was observed to travel from the chamber with the negative electrode to the chamber contacting the positive electrode, resulting in white resin at the former electrode. The electrode polarities were then reversed and the color was seen to shift to the other side, indicating that pressure was able to modulate the affinity of the ion-exchange resin. This demonstrates that nucleic acid molecules can be transported electrophoretically in an ion-exchange medium in the presence of low salt buffer at hyperbaric pressure to concentrate the sample.

EXAMPLE 9
Purification of Nucleic Acids from Cells or Viruses by Hyberbaric Permeabilization and Electrophoresis.

A 5 ml culture of *E. Coli* cells containing a PACYC plasmid is grown to an optical density of 0.6 at 600 nm in Luria broth supplemented with 100 µg/ml of ampicillin (LB/amp). One milliliter of the culture was centrifuged at 10,000 g for 10 minutes to pellet the cells. The supernatant was discarded and the cells were resuspended in 1 ml of distilled water. 90 µl of the resuspended cells and 2 µl of 384 µM rhodamine conjugated 21-mer oligonucleotide were loaded into a high-pressure electrophoresis cartridge. as described in Example 8. A 1% agarose gel was formed in another chamber of the cartridge. The cartridge was pressurized to 30,000 psi and a 35 V electric field was applied for 15 minutes. The labeled oligonucleotide was observed to have moved into the gel, indicating that the electrical process was adequate for the movement of DNA. The agarose plug was removed with a needle and placed into the well of an agarose slab gel. The slab gel was run with four control lanes: one containing a pure plasmid, another containing untreated cells, one containing cells which had been subjected to electrophoresis in the cartridge at atmospheric pressure and the last contained cells that have been pressurized to 30,000 psi for 15 minutes without electrophoresis. The results showed that high pressure can release plasmid DNA by permeabilizing the cell walls and membranes. This result indicates the possibility that plasmid DNA can be purified in a single-step process. Separate steps are not required for lysis, neutralization, and purification

EXAMPLE 10

Cell Lysis and RNA Purification by Pressure Pulsing and/or Constant Pressure

Murine NIH 3T3 cells were grown on tissue culture dishes according to standard methods. Cells in the tissue culture plate were washed twice with 8 ml of phosphate buffered saline (PBS), lifted, and resuspended in 500 ml of PBS. 50 μl of the cell mixture was placed in hollow capsules, which were inserted into pressure chambers filled with silica melting point oil (Sigma Chemicals, St. Louis, Mo.). The capsules containing the cell solution were pressurized and depressurized sixty times. In each cycle, the capsules were pressurized to 30,000 psi for 1.25 seconds and returned to atmospheric pressure for 1.25 seconds. In a second experiment, the capsules were kept at a constant 60,000 psi for 10 minutes.

To determine the extent of cell lysis, a portion of the cell lysis solution was removed from the capsule and observed in a phase contrast optical Olympus microscope. Compared to the unpressurized control cells, the pressurized cell solution was found to contain fragmented cells and cellular debris despite the existence of a large number of intact cells. 20 μl aliquot from each sample were mixed with 200 μl of OliGreen solution (diluted 1:1,000) (Molecular Probes, Eugene, Oreg.). Fluorescence emission intensities at 530 nm were detected with an excitation wavelength of 485 nm. The results indicated a 10-fold increase in fluorescence intensity for the cells lysed by both pulsing and constant pressurization. Nucleic acid products in the cell solution were also examined using 1% agarose gel electrophoresis. The results showed that the majority of the nucleic acid in the supernatant of the pressurized cell solutions was RNA, as determined by the presence of 28S and 18S rRNA. This hypothesis was confirmed by a QIAamp purification test, assuming that DNA binds to QIAamp membrane and RNA does not.

As a positive control, total RNA released from NIH 3T3 cells by either pressure pulsing or pressing was purified using RNeasy kit #74103 (Qiagen, Santa Clarita, Calif.). RNA products isolated from the hyperbaric pressure purification or the RNeasy kit were analyzed by agarose gel electrophoresis. The results indicated that the outer membranes of cells are destroyed by hyperbaric pressure pulsing and/or pressing. RNA released by pressure lysis is similar to RNA released by the conventional method. Thus, RNA molecules released in the pressurization process allow the cooperation of cell lysis and RNA purification in a single step purification process.

EXAMPLE 11

Cell Lysis and Genomic DNA Purification by Hyperbaric Pressure Pulsing and/or Constant Pressure Pressing In addition to the disruption of cells by applying high pressure pulsing and/or constant pressure pressing as described in Example 10, additional agents (e.g., proteinase K, detergents) can be supplemented to aid in the release of genomic DNA from DNA/protein complexes in the nuclei. Neutral or positively charged detergents are tested, as these compounds are compatible with the downstream high pressure purification. Such detergents include NP-40 and cetyl-trimethylammonium chloride (CTMA). Initially, DEAE resin is activated with 2% NP-40, 100 mM sodium acetate buffer, pH 4.5 and equilibrated with a buffer of 50 mM TrisCl, 400 mM NaCl, 2% NP-40, pH 8.5. Then, murine NIH 3T3 cells were washed with 8 ml PBS twice, lifted in 1 ml PBS and loaded onto the DEAE column as described in Example 1. High pressure pulsing and/or constant pressing is applied to the cartridge; as described in Example 10. Elution of the genomic DNA is achieved by electroelution at 35,000 psi. As a quantity and quality control, 200 μl lifted NIH 3T3 cells were mixed with 200 μl sucrose buffer (i.e., 1.28 M sucrose, 40 mM Tris-Cl, 20 mM $MgCl_2$, 4% triton X-100, pH 7.4). After the mixture was centrifuged at 2,000 rpm for 15 minutes and the supernatant was discarded, 400 μl of general lysis buffer (i.e., 0.8 M guanidine HCl, 30 mM Tris-HCl, 30 mM EDTA, 5% Tween-20, 0.5% Triton X-100, pH 8.0) was added, vortexed briefly, and followed by a proteinase K digestion reaction at 55° C. for one hour. After the digestion, the lysis solution was centrifuged at 14,000 rpm for 10 minutes. 200 μl supernatant was then collected and nucleic acid purified using protocol described in QIAamp Tissue kit #29304. Purified nucleic acid was finally eluted in 100 μl distilled water. The nucleic acid content of this solution was analyzed using the standard OliGreen assay. If the fluorescence intensity of the control is found to be similar to that of the cells that have been pressurized, this example would suggest that the two types of pressurization treatments are as efficient as the conventional method.

These pressurization lysis procedures were also applied in the lysis of yeast (S. cerevislae). First, yeast culture cells were grown either over night or for 3 hours. 1 ml of cell cultures were washed twice with 1 ml of TN buffer (20 mM Tris-HCl, pH 7.4, 100 mM NaCl), pelleted, and resuspended in 1 ml of TN buffer with 1 mM EDTA (TNE buffer). 50 μl aliquots of the yeast in the TNE solution were placed in hollow capsules and pressurized either to 30,000 psi, with 2.5 second pressurization and depressurization steps repeated 240 times, or using 60,000 psi constant pressure for 10 minutes. To determine the amount of nucleic acid released by pressurization, OliGreen assays were performed. The results showed that there were two- to four-fold increases in fluorescence for the pressurized yeast as compared to the untreated cells. To improve the lysis efficiency, glass beads (300μ) were added to the yeast TNE solution and the mixture was vortexed for 2 minutes, prior to the hyperbaric pressure lysis steps. However, no significant changes in the yield of nucleic acids were observed. As in the lysis method used for the NIH 3T3 cells mentioned above, addition of detergent molecules is required to break the nuclei and release the genomic DNA. As a positive control, yeast cells were also lysed using standard lyticase and proteinase K enzymatic lysis procedures (Qiagen Genome DNA Purification Manual, Santa Clarita, Calif.). The nucleic acids were then purified using QIAamp Tissue kit #29304 (Qiagen, Santa Clarita, Calif.). The level of nucleic acids obtained was analyzed using agarose gel electrophoresis and OliGreen binding assay. The results indicated that both the control method and the pressure lysis procedure yielded a similar amount of nucleic acid.

EXAMPLE 12

DNA DNase I Fragment Purification in an Anion-Exchange Cartridge

To obtain random digested, various-length DNA fragments (e.g., from genomic DNA), a method based on anionexchange chromatography is carried out. A rapid DNA fragmentation is started with a purified biological sample and followed by repeated hyperbaric pressure anion exchange and in combination of DNase I digestion. Thus, human blood is lysed and purified in an anion-exchange cartridge as described in Example 7, and genomic DNA elutes off from the column at 45,000 psi in a buffer that has 100 mM NaCl, 50 mM Tris-Cl, pH 7.4. This solution is then mixed with DNase I (Pharmacia, Piscataway, N.J.) and incubated at 37° C. for various lengths of time. To inactive the DNase I, the digestion solution is either heated at 90° C. for 3 minutes or EDTA is added to a final concentration of 25 mM. Alternatively, the DNA digestion solution is loaded onto a new DEAE cartridge for a second step purification without inactivating DNase I. The heat- or EDTA-treated solution is then loaded onto a new DEAE cartridge (can be the same or simplified as used in genome DNA purification). The digested DNA fragments are then eluted with 100 µl of a buffer containing 100 mM NaCl, 50 mM Tris-Cl, pH 7.0 at 40,000 psi. The size distribution of the resulting DNA fraction can be analyzed by agarose gel electrophoresis. This sample preparation method can be incorporated in DNA hybridization chips, allowing a single step sample preparation and downst ream hybridization an alysis. 1% agarose gel electrophoresis is used to evaluate the size distributions of the DNA fragments.

EXAMPLE 13

Figure 10B:
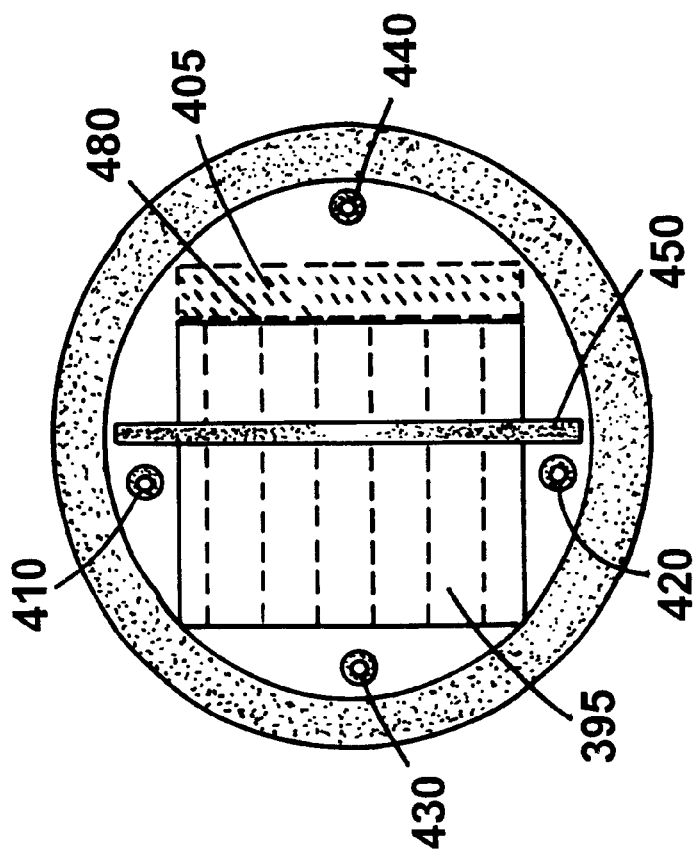
FIGS. 10A and 10B are side and top views, respectively, of a high pressure purification cartridge.
Figure 10A:
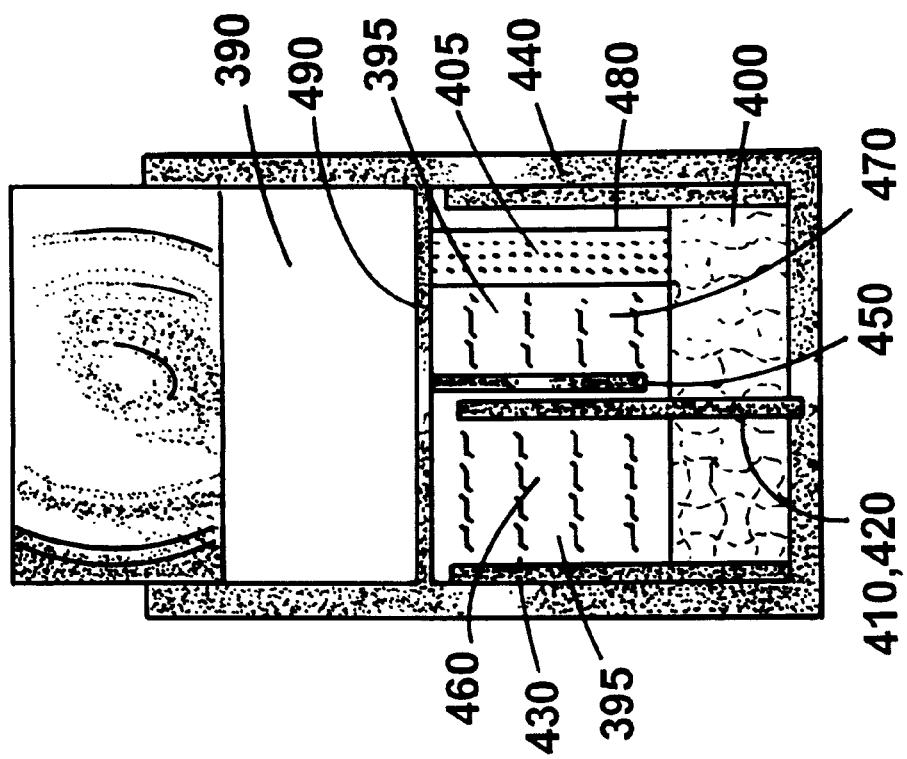

A Cartridge for Integrated High Pressure-Mediated Cell Lysis and Nucleic Acid Purification The designed cartridge is composed by four essential compartments as illustrated in FIGS. 10A and 10B. The starting materials (e.g., cell solutions or cell lysis solutions) are loaded into compartment 390. Compartment 395 (including a first half 460 and a second half 470) is filled with an ion-exchange resin such as DEAE on solid support for nucleic acid purification. This compartment is also accessible to four electrodes, 410, 420, 430, and 440, which are protected by polyacrylamide gel. Electrodes 410 and 420 are used during pre-elution purification under relative low pressure to remove contaminants (e.g., proteins, polysaccharides, and lipids). Electrodes 430 and 440 are used when nucleic acid products are extracted under high pressure. All of the electrodes can be used in the lysis step as described in Examples 10 and 11. Compartment 395 is separated by a plastic wall 450, which allows nucleic acid molecules travel from the first half 460 to the second half 470 such that resolution can be improved by introducing chromatographic effects. For example, high resolution can be achieved based on both the charge and the size of the nucleic acids. Since larger DNA requires higher pressure to release from the resin, relatively small DNA molecules will be eluted off at first, at the appropriate pressure. The chromatographic effect enhances the separation of different sizes of DNA. Compartment 400 contains layers of absorptive materials (e.g., cellulose-based filter membranes, silica gels, CaO, and cotton). The adsorptive material helps in absorbing extra fluids and thus relatively large quantities of solution can be introduced into the cartridge so that the yield of the product can be improved. Compartment 405 is separated from compartments 395 and 400 by a nucleic acid permeable membrane 480, and contains a low salt buffer (i.e., 50 mM NaCl, 50 mM Tris-HCl, pH 8.5). Although compartment 405 is physically separated from compartment 390, the barrier 490 between the can be punched through using a needle, and the nucleic acid product can be collected with a syringe.

In the operation of the cartridge, biological samples, e.g., blood, cell culture and homogenized plant or tissue cultures, are injected into compartment 390. Then, the cartridge is transferred into a pressure modulation apparatus, in which the electrodes 410, 420, 430, and 440 are attached to voltage sources and voltage changes are computer controlled. The pressure is increased to 60,000 psi. At this pressure, cell fluid saturates the resin and the absorptive materials in compartments 395 and 400. Simultaneously, the cells are lysed and the nucleic acids bind to the resin. After holding at high pressure for a short period of time, pressure is decreased to 10,000 psi. Electrodes 410 and 420 are turned on. At this pressure level, proteins and other contaminant molecules to which the resin does not bind will travel towards the electrodes and be trapped in the polyacrylamide gel surrounding these electrodes. Once purification is complete, the pressure in the chamber is increased, and nucleic acid product collection begins. For example, the pressure is increased to 23,000 psi to collect RNA sample, 35,000 psi to collect plasmid, and 45,000 psi to collect genomic DNA. The nucleic acid products are gathered in compartment 405 by turning on electrodes 430 and 440. Once elution finishes, the pressure is decreased, and the cartridge is removed from the pressure modulation apparatus. The nucleic acid products are recovered by punching a needle into compartment 405 and collecting the nucleic acids with a syringe.

EXAMPLE 14

Cell Lysis Assisted by Pumping High Pressure Air

50 µl of an overnight yeast cell culture was loaded onto a 500 ml column. A piston was inserted into the column, allowing external pressure to be transmitted to the column. The column was transferred to a pressure modulation apparatus and then pressurized to 60,000 psi for 5 minutes, depressurized, kept at atmospheric pressure for 1 minute and pressurized again. After two more depressurization/pressurization cycles, the cell solution was removed from the column at atmospheric pressure. A microscopic examination was conducted, and the nucleic acid content was estimated using fluorescence dye binding assay. The results indicated that high pressure air pumping afforded a similar level of cell lysis as that achieved through high pressure pulsing.

EXAMPLE 15

Separation of RNA from an RNA/DNA Mixture

Total RNA from Torula Yeast (Type IV) was purchased from Sigma (St. Louis, Mo.). pKK223-3 (Pharmacia, Piscataway, N.J.) was used as the DNA control. The RNA and DNA were mixed in an NTM buffer solution, pH 7.0 (NTM: 175 mM NaCl, 35 mM Tris, 0.5 mM $MgCl_2$). The mixture was prebound to a Qiagen DEAE resin in a stainless steel cartridge. 0.4 ml of the RNA/DNA solution was injected into a cartridge containing activated DEAE resin, followed by washing with 200 µl of NTM buffer, pH 8.5. 1200 µl elution fractions were collected at 23,600 psi in NTM, pH 8.5. The cartridge was washed with 1 ml of high salt buffer (1.25 M NaCl, 50 mM Tris-HCl, pH 8.5, 15% ethanol). The elutions were analyzed using OliGreen fluorescence assay. The remaining elution fractions and high salt buffer wash solutions were ethanol precipitated and dissolved in 20 µl double distilled water. These were checked by agarose gel electrophoresis. The results indicated that the RNA was completely separated from the DNA and RNA is purified. The DNA was recovered in the high salt washing step with little RNA contamination. Thus, RNA can be separated from an RNA/DNA mixture by high pressure-mediated purification.

Other Embodiments

From the description above, one skilled in the art can ascertain the essential characteristics of the invention and without departing from the spirit and scope thereof, can make various changes and modifications of the invention to adapt it to various usages and conditions.

It is to be understood that while the invention has been described in conjunction with the detailed description thereof, that the foregoing description is intended to illustrate and not to limit the scope of the appended claims. Other aspects, advantages, and modifications are within the scope of the following claims.

What is claimed is:

1. A method for purifying nucleic acids from a sample, said method comprising:
   providing a pressure-modulation apparatus, said apparatus comprising an electrode array system comprising at least two electrodes; and a conduit interconnecting said electrodes, wherein said conduit contains an electrically conductive fluid in contact with a phase positioned in a pressure chamber,
   contacting the sample with said phase at an initial pressure, wherein said phase non-specifically binds to nucleic acids with greater affinity than said phase binds to non-nucleic acid components of the sample;
   transporting at least some of the non-nucleic acid components towards one of said electrodes;
   modifying the pressure to a level sufficient to disrupt the binding of the nucleic acids to the phase; and transporting the nucleic acids towards a second of said electrodes.

2. A method for purifying nucleic acids from a sample, said method comprising:
   providing a pressure-modulation apparatus, said apparatus comprising an electrode array system comprising at least two electrodes; and a conduit interconnecting said electrodes, wherein said conduit comprises an electrophoretic capillary and contains an electrically conductive fluid in contact with a phase positioned in a pressure chamber,
   contacting the sample with said phase at an initial pressure, wherein said phase non-specifically binds to nucleic acids with greater affinity than said phase binds to non-nucleic acid components of the sample;
   electrophoretically separating at least some of the non-nucleic acid components from the nucleic acids;
   modifying the pressure to a level sufficient to disrupt the binding of the nucleic acids to the phase; and
   electrophoretically separating the nucleic acids from the phase at the modified pressure.

3. A method for purifying nucleic acids from a sample, said method comprising:
   providing a pressure-modulation apparatus, said apparatus comprising an electrode array system comprising at least two electrodes; and a conduit interconnecting said electrodes, wherein said conduit comprises an electroosmotic capillary and contains an electrically conductive fluid in contact with a phase positioned in a pressure chamber;
   contacting the sample with said phase at an initial pressure, wherein said phase non-specifically binds to nucleic acids with greater affinity than said phase binds to non-nucleic acid components of the sample;
   electroosmotically separating at least some of the non-nucleic acid components from the nucleic acids;
   modifying the pressure to a level sufficient to disrupt the binding of the nucleic acids to the phase; and
   electroosmotically separating the nucleic acids from the phase at the modified pressure.

4. A method for isolating and purifying nucleic acids from a sample, said method comprising:
   applying the sample to a phase at an initial pressure, wherein said phase non-specifically binds to nucleic acids with greater affinity than said phase binds to non-nucleic acid components of the sample;
   spatially separating at least some of the non-nucleic acid components from the phase and the nucleic acids;
   modifying the pressure to a level sufficient to disrupt the binding of at least some of the nucleic acids to the phase; and
   spatially separating the nucleic acids from the phase at the modified pressure, wherein the applying and first spatially separating steps are carried out within a single reaction vessel.

5. The method of claim 4, wherein the first spatially separating step comprises transporting non-nucleic acid components into a reservoir.

6. The method of claim 5, wherein the reservoir contains a binding material.

7. The method of claim 4, wherein the first spatially separating step comprises electrophoresis.

8. The method of claim 4, wherein the first spatially separating step comprises electroosmosis.

9. The method of claim 4, wherein said initial pressure is ambient pressure and said modified pressure is an elevated pressure.

10. The method of claim 9, wherein said elevated pressure is 500 to 100,000 psi.

11. The method of claim 4, wherein the sample comprises cells and said method further comprises subjecting said sample to a hyperbaric pressure sufficient to lyse the cells.

12. The method of claim 11, wherein the cells comprise external and nuclear membranes, and the hyperbaric pressure is sufficient to lyse the external membrane, but insufficient to lyse the nuclear membranes.

13. The method of claim 4, wherein the sample comprises nucleic acid-binding proteins and said method further comprises subjecting said sample to a hyperbaric pressure sufficient to inactivate the nucleic acid-binding proteins.

14. The method of claim 13, wherein the nucleic acid-binding proteins comprise nuclease enzymes.

15. The method of claim 4, wherein the sample comprises various sizes of nucleic acids, the modified pressure level is sufficient only to disrupt the binding of relatively small nucleic acids to the phase, and the method further comprises:
   further modifying the pressure to a level sufficient to disrupt the binding of relatively larger nucleic acids to the phase; and
   spatially separating the nucleic acids from the phase at the further modified pressure.

16. The method of claim 11, wherein said sample comprises a biological fluid.

17. The method of claim 11, wherein said sample comprises whole blood.

18. The method of claim 11, wherein said sample comprises serum.

19. The method of claim 11, wherein said sample comprises cultured cells.

20. The method of claim 11, wherein said sample comprises tumor biopsy tissue.

21. The method of claim 11, wherein said sample comprises plant tissue.

22. The method of claim 11, wherein said sample comprises living tissue.

23. The method of claim 4, wherein said nucleic acids comprise DNA.

24. The method of claim 4, wherein said nucleic acids comprise total RNA.

25. The method of claim 4, wherein said nucleic acids comprise messenger RNA (mRNA).

26. The method of claim 4, wherein said nucleic acids comprise viral RNA.

27. The method of claim 23, wherein said DNA is chromosomal DNA.

28. The method of claim 23, wherein said DNA comprises a vector.

29. The method of claim 23, wherein said DNA comprises viral DNA.

30. The method of claim 4, wherein said modified pressure is sufficient to elute vector DNA but not high enough to elute chromosomal DNA.

31. The method of claim 4, wherein said modified pressure is sufficient to elute RNA but not high enough to elute chromosomal DNA.

32. The method of claim 4, wherein said method further comprises adding a dicarbonyl compound to the sample to inactivate nucleic-acid binding proteins.

33. The method of claim 4, wherein said phase comprises hydroxyapatite.

34. The method of claim 4, wherein said phase comprises an immobilized nucleic acid molecule.

35. The method of claim 4, wherein said phase comprises silica.

36. The method of claim 4, wherein said phase comprises an anion-exchange resin.

37. The method of claim 4, wherein said phase comprises a pressure-sensitive gel.

38. The method of claim 4, wherein said phase comprises a pressure-stable medium.

39. The method of claim 38, wherein said medium is a non-porous resin comprising 1 to 50 µm beads having a positively charged surface.

40. The method of claim 4, further comprising concentrating the nucleic acids between two membranes by electrophoresis, wherein one of said membranes is substantially impermeable to nucleic acids and the second membrane has increased permeability to nucleic acids under applied electrical potential.

41. The method of claim 40, wherein said concentration is carried out at said modified pressure.

42. The method of claim 4, further comprising trapping the spatially separated nucleic acids in a filter by electrophoresis.

43. The method of claim 4, further comprising transporting the spatially separated nucleic acids to an analytical device.

44. The method of claim 43, wherein said analytical device is a matrix-assisted laser desorption and ionization (MALDI) mass spectrometer.

45. A device for carrying out the method of claim 4, the device comprising:

a pressure modulation apparatus; and a pressurizable cell containing said phase, wherein said cell is adapted to fit within said apparatus.

* * * * *